United States Patent
Tulley et al.

(10) Patent No.: US 11,437,145 B2
(45) Date of Patent: Sep. 6, 2022

(54) AUGMENTED INTELLIGENCE FOR NEXT-BEST-ACTION IN PATIENT CARE

(71) Applicant: Recovery Exploration Technologies Inc., San Francisco, CA (US)

(72) Inventors: Carl Bate Tulley, San Fransico, CA (US); Robert Derward Rogers, Oakland, CA (US); Jennifer May Lee, London (GB); David A. Epstein, Croton-on-Hudson, NY (US); Michelle S. Keller, Los Angeles, CA (US); Wian Stipp, Somerleyton (GB); David Robinson, Santa Cruz, CA (US); Matthew McSorley, Pittsburgh, PA (US)

(73) Assignee: RECOVERY EXPLORATION TECHNOLOGIES INC., San Francisco, CA (US)

( * ) Notice: Subject to any disclaimer, the term of this patent is extended or adjusted under 35 U.S.C. 154(b) by 0 days.

(21) Appl. No.: 17/406,604

(22) Filed: Aug. 19, 2021

(65) Prior Publication Data
US 2022/0059224 A1  Feb. 24, 2022

Related U.S. Application Data

(60) Provisional application No. 63/067,774, filed on Aug. 19, 2020.

(51) Int. Cl.
*G06F 16/28* (2019.01)
*G06N 20/00* (2019.01)
(Continued)

(52) U.S. Cl.
CPC ............ *G16H 50/20* (2018.01); *G10L 15/22* (2013.01); *G10L 15/26* (2013.01); *G10L 25/66* (2013.01);
(Continued)

(58) Field of Classification Search
CPC ........ G16H 50/20; G16H 10/40; G16H 10/60; G16H 40/20; G16H 50/70; G16H 70/20;
(Continued)

(56) References Cited

U.S. PATENT DOCUMENTS 10,446,273 B1 * 10/2019 McNair ................. G16H 15/00
2009/0192800 A1    7/2009 Brandt
(Continued)

FOREIGN PATENT DOCUMENTS

| WO | 01/069513 | 9/2001 |
| WO | 2012122198 | 9/2012 |
| WO | 2020006495 | 1/2020 |

OTHER PUBLICATIONS

International Search Report and Written Opinion of the International Searching Authority, International Application No. PCT/US2021/046702, dated Dec. 8, 2021.

*Primary Examiner* — Maroun P Kanaan
(74) *Attorney, Agent, or Firm* — Beyer Law Group LLP

(57) ABSTRACT

A next-best-action system includes real-time operation and off-line training and processes. During off-line training databases of medical conditions and associated diagnostic factors, tests and treatments are used to create models used for later natural language processing of input electronic text. Diagnostic factors are ranked according to the probability that they indicate conditions and are stored in a matrix. Treatments corresponding to conditions are also stored in a matrix. During real-time operation electronic text is received from patient history of an EHR system, from a transcribed conversation between a physician and a patient, or from input that the physician makes in the EHR system or in an overlaid diagnostic user interface. The electronic text is processed by an NLP pipeline that derives clinical diagnostic factors and test results for the patient. The factors and test results are matched against the matrix of factors to produce
(Continued)

a list of likely conditions, along with an ordered list of factors and tests that are either unknown or not yet performed for that patient.

30 Claims, 23 Drawing Sheets

(51) Int. Cl.
| | |
|---|---|
| *G16H 50/20* | (2018.01) |
| *G16H 40/20* | (2018.01) |
| *G16H 10/40* | (2018.01) |
| *G16H 10/60* | (2018.01) |
| *G16H 50/70* | (2018.01) |
| *G16H 70/20* | (2018.01) |
| *G10L 15/22* | (2006.01) |
| *G10L 15/26* | (2006.01) |
| *G10L 25/66* | (2013.01) |
| *G06F 40/295* | (2020.01) |
| *G06F 40/30* | (2020.01) |

(52) U.S. Cl.
CPC ............. *G16H 10/40* (2018.01); *G16H 10/60* (2018.01); *G16H 40/20* (2018.01); *G16H 50/70* (2018.01); *G16H 70/20* (2018.01); *G06F 40/295* (2020.01); *G06F 40/30* (2020.01)

(58) Field of Classification Search
CPC ......... G10L 15/22; G10L 15/26; G10L 25/66; G06F 40/295; G06F 40/30
See application file for complete search history.

(56) References Cited

U.S. PATENT DOCUMENTS

| | | |
|---|---|---|
| 2010/0145720 A1 | 6/2010 | Reiner |
| 2011/0119212 A1* | 5/2011 | De Bruin ................. A61B 5/00 706/12 |
| 2014/0201627 A1 | 7/2014 | Zoll |
| 2020/0211692 A1* | 7/2020 | Kalafut ................... G06N 20/00 |
| 2021/0142904 A1* | 5/2021 | Michuda ................ G16H 70/60 |

* cited by examiner

| |
|---|
| Ankylosing spondylitis |
| Treatments          <u>300</u> |
|     ACUTE |
| adults with pain and/or stiffness ~ 310 |
|    1st line ⌄ nonsteroidal anti-inflammatory drug + nonpharmacologic therapy<br><br>   Adjust ⌄ analgesic<br><br>• with local intra-articular inflammation or enthesitis<br>   <u>Plus</u> ⌄ intra-articular corticosteroid injection<br>• with peripheral joint involvment<br>   <u>Plus</u> ⌄ sulfasalazine or methotrexate |
| adults without pain and/or stiffness ~ 320 |
|    1st line ⌄ re-assessment and observation<br><br>                                                                                            330 |
|     ONGOING |
| adults with pain and/or stiffness refractory to 2 NSAIDs and nonpharmacologic measures |
|    1st line ⌄ tumor necrosis factor (TNF) alpha inhibitor + physical theraphy<br><br>   Adjunct ⌄ continued nonsteroidal anti-inflammatory drug<br><br>   2nd line⌄ secukinumab or ixekizumab<br><br>   Adjunct ⌄ continued nonsteroidal anti-inflammatory drug<br><br>   2nd line⌄ alternative tumor necrosis factor (TNF) alpha inhibitor + physical therapy<br><br>   Adjunct ⌄ continued nonsteroidal anti-inflammatory drug |

*FIG. 4*

Addition of Clinical Note

FIG. 5

702 — Ankylosing spondylitis

History and examination

Key diagnostic factors — 704

COMMON

- HLA-B27 positive
- inflammatory back pain
- iritis/uveitis
- enthesitis
- presentation in late teens and early 20s
- male sex
- positive family history of AS Other diagnostic factors — 706

COMMON

- fatigue
- sleep disturbances
- HLA-B27
- endoplasmic reticulum aminopeptidase 1 (ERAP1) and interleukin-2e receptor (IL23R) genes
- positive family history of AS
- male sex

WEAK

- Klebsiella pneumoniae — 708

FIG. 9A

702 — Ankylosing spondylitis

Investigations investigations to order — 712

- pelvic x-ray

Investigations to consider — 714

- HLA-B27
- MRI
- cervical spine x-ray (lateral)
- lumbar spine x-ray (lateral)
- Thoracic spine x-ray (lateral)
- ultrasound

FIG. 9B

| Calendar | Flow Board | Recall Board | Messages | Patient/Client | Fees | Modules | Procedures | Administration | Reports | Miscellaneous | Popups | About | Jennifer Lee |
|---|---|---|---|---|---|---|---|---|---|---|---|---|---|

Patient: None

◄ Calendar ✱ ⊞ ✕ | Patient Finder ✱ ⊞ ✕ — 802

Patient Finder ⁕ ⊕

[+ New Patient]

Show 10 ▾ entries                                                                          Search

| Search by Name | Search by Home Phone | Search by SSN | Search by Date of Birth | Search by External ID |
|---|---|---|---|---|
| ◦ Full Name | ◦ Home Phone | ◦ SSN | ◦ Date of Birth | ◦ External ID |
| Davis, Jordan | | | 1958-03-01 | 99998888 |
| Green, Ben | | | 1975-12-12 | 99993333 |
| Houston, Max | 804 | | 1980-04-01 | 9 |
| Jones, Martha | | | 1949-04-02 | 99991111 |
| Larsen, Emily | | | 1994-05-10 | 11 |
| Miller, Adrian | | | 1965-07-15 | 99997777 |
| Ortez, Cassandra | | | 1983-03-06 | 99992222 |
| Ridge, Ana | | | 1957-12-01 | 99994444 |
| Rodriquez, Jessica | | | 1960-05-12 | 99996666 |
| Swanson, Heather | | | 1957-05-15 | 10 |

Open in New Window   Search with exact method

Showing 1 to 10 of 11 entries                                                    Prev [1] 2 Next

800

501

Example Interaction
*FIG. 10A*

Calendar  Flow Board  Recall Board  Messages  Patient/Client  Fees  Modules  Procedures  Administration  Reports  Miscellaneous  Popups  About       Jennifer Lee Patient: None ◄ Calendar ⚙ ● × | Patient Finder ⚙ ● × |— 802                                         800                                               Search by any q Patient Finder ⁂ ⚙
[+ New Patient]

| | | Patient |
| --- | --- | --- |
| | | DQR |
| | | MRN |

811

Differential Diagnoses

500

Show 10 ● entries

| Search by Name | Search by Home Phone | Search by SSN | Search by Date of Birth |
| --- | --- | --- | --- |
| Full Name | ‑ Home Phone | ‑ SSN | ‑ Date of Birth |
| Davis, Jordan | | | 1958-03-01 |
| Green, Ben | | | 1975-12-12 |
| Houston, Max | | 804 | 1980-04-01 |
| Jones, Martha | | | 1949-04-02 |
| Larsen, Emily | | | 1994-05-10 |
| Miller, Adrian | | | 1965-07-15 |
| Ortez, Cassandra | | | 1983-03-06 |
| Ridge, Ana | | | 1957-12-01 |
| Rodriquez, Jessica | | | 1960-05-12 |
| Swanson, Heather | | | 1957-05-15 |

[Differential]  [Factors]  [Tests]  —501

Open in New Window  Search with exact method

Showing 1 to 10 of 11 entries                                                                   1  2  Next Example Interaction
FIG. 10B

Example Interaction

FIG. 10C

Calendar   Flow Board   Recall Board   Messages   Patient/Client   Fees   Modules   Procedures   Administration   Reports   Miscellaneous   Popups   About — □ ×

Patient: Heather Swinson ×
DOB: 1957 05 15 Age: 64                                 ↻ + Open Encounter None   800                              Jennifer Lee
                                                        View Past Encounters (2) ▾                                Search by any dx ◂ Calendar ⊘ 6 ×   Patient Finder ⊘ 6 ×   Dashboard ⊘ 6 ×   Past Encounters and Documents ⊘ 6 ×

Medical Record Dashboard – Heather Swinson        810

Dashboard   History   Report   Documents   Transactions   Issues   Ledger   External Data Billing                                                              ID Card/Photos expand
Edit Demographics collapse                                           Edit Clinical Reminders collapse
  Who │ Contact │ Choices │ Employer │ Stats │ Misc │ Guardian          Measurement Weight [Past Due]
    Name: ⊙ Heather Swinson       External ID: 1C                       Assessment Colon Cancer Screen
    DOB: 1957/05/15                      Sex: Female                    Measurement Mammogram [Pa
    S.S.: ⊙                       License ID:                           Treatment Influenza Vaccine [Pa
    Marital Status:                                                     Assessment Tobacco [Past Due]
    User Defined:                                                    Add Appointments collapse
    Billing Note:                                                       No Appointments
                                                                        No Recall
                                                                     Recurrent Appointments
Edit Messages expand                                                    None
Edit Patient Reminders expand                                        Edit Medical Problems collapse
Edit Disclosures expand                                                 Nothing Recorded
Edit Amendments expand                                               Edit Allergies collapse
Labs collapse                                                           Nothing Recorded
  No lab data documented                                             Edit Medications collapse
Vitals collapse                                                         Nothing Recorded
  No vitals have been documented                                     Edit Immunizations collapse
                                                                        None
                                                                     Edit Perscriptions collapse ⊙ Heather Swinson                                     500  ×
DOB: 1957 05 15 Age: 64
Differential Diagnoses                                   824
< Back to overview Coronavirus disease 2019                         +        838
(COVID-19) >                          44

Pertinent Factors fever                            +
cough                            +
dyspnea                          +
myalgia                          +
sore throat                      +
headache                         ⊙
rhinorrhea
chest pain                       ⊙⊙
hemoptysis                       +
diabetes Are these present?                                        839
altered sense of taste
altered sense of smell
fatigue
arthralgia
sputum expectoration
sputum production

[Differential]   [Factors]   [Tests]
    832    834    836

⟨Dx⟩ ∨
                                                          501

Example Interaction

FIG. 10D

Calendar  Flow Board  Recall Board  Messages  Patient/Client  Fees  Modules  Procedures  Administration  Reports  Miscellaneous  Popups  About — □ ×

Patient: Heather Swinson ×
DOB: 1957 05 15 Age: 64   ⟲ + Open Encounter None   800   Jennifer Lee  (Search by any dx)
View Past Encounters (2) ▾

◂ Calendar ⌀ ₆ × | Patient Finder ⌀ ₆ × | Dashboard ⌀ ₆ × | Past Encounters and Documents ⌀ ₆ ×

Medical Record Dashboard -- Heather Swinson       810

Dashboard  History  Report  Documents  Transactions  Issues  Ledger  External Data Billing
Edit Demographics collapse

| Who | Contact | Choices | Employer | Stats | Misc | Guardian |

Name: ⊙ Heather Swinson   External ID: 1C
DOB: 1957/05/15            Sex: Female
S.S.: ⊙                    License ID:
Marital Status:
User Defined:
Billing Note:

ID Card/Photos expand
Edit Clinical Reminders co

Measurement Weight [Past Due]
Assessment Color Cancer Scree
Measurement Mammogram [Pas
Treatment Influenza Vaccine [Pa
Assessment Tobacco [Past Due]

Add Appointments collapse
No Appointments
No Recall
Recurrent Appointments

None
Edit Medical Problems col
Nothing Recorded
Edit Allergies collapse
Nothing Recorded
Edit Medications collapse
Nothing Recorded
Edit Immunizations collapse
None
Edit Perscriptions collapse Edit Messages expand
Edit Patient Reminders expand
Edit Disclosures expand
Edit Amendments expand
Labs collapse
No lab data documented
Vitals collapse
No vitals have been documented ┌─────────────────────────────────────────────┐   ╮
│                                     500      │   │ 842
│ ⓘ Heather Swinson              ×        │   │
│   DOB: 1957 05 15 Age: 64                   │   │
│ Differential Diagnoses                  │   ╯
│ ‹ Back to overview                          │   ╮
│                                             │   │ 844
│ real-time reverse transcription      ⟲      │   │
│ polymerase chain reaction tRT-              │   │
│ PCRI                                        │   │
│                                             │   │
│ pulse oximetry                       ⟲      │   │
│                                             │   │
│ ABC                                  ⟲      │   │
│                                             │   │
│ CBC                                  ⟲      │   │
│                                             │   │
│ comprehensive metabolic panel        ⟲      │   │
│                                             │   │
│ blood glucose level                  ⟲      │   │
│                                             │   │
│ coagulation screen                   ⟲      │   │
│                                             │   │
│ cardiac biomarkers                   ⟲      │   │
│                                             │   │
│ serum C reactive protein             ⟲      │   │
│                                             │   │
│ serum erythrocyte                    ⟲      │   │
│ sedimentation rate                          │   │
│                                             │   │
│ serum lactate dehydrogenase          ⟲      │   │
│                                             │   │
│ serum interluekin-6 level            ⟲      │   │
│                                             │   │
│  [Differential]   [Factors]   [Tests⁺]      │   │
│      832           834          836         │   │
└─────────────────────────────────────────────┘

[Dx]  ◂
                                          501

Example Interaction
*FIG. 10E*

Calendar  Flow Board  Recall Board  Messages  Patient/Client  Fees  Modules  Procedures  Administration  Reports  Miscellaneous  Popups  About           — □ ×
Patient: Heather Swinson ×                                                                                                                                Jennifer Lee
DOB: 1957 05 15 Age: 64          ⟲ + Open Encounter None  800                                                                                             (Search by any d⟲)
                                 View Past Encounters (2) ▾

◂Calendar ⌕ 🖉 ×  Patient Finder ⌕ 🖉 ×  Dashboard ⌕ 🖉 ×  Past Encounters and Documents ⌕ 🖉 ×

Medical Record Dashboard – Heather Swinson         810                                                                ⎫
                                                                                                                      ⎬ 811
Dashboard  History  Report  Documents  Transactions  Issues  Ledger  External Data                                    ⎭

Billing                                                    ID Card/Photos expand              ┌─────────────────────────────────────────────×─┐
[Edit] Demographics collapse                               [Edit] Clinical Reminders co       │  500 ⎫                                          │
 Who | Contact | Choices | Employer | Stats | Misc | Guardian    Measurement Weight [Past Due]│  ⓘ Heather Swinson                             │
                                                           Assessment Color Cancer Scree      │     DOB: 1957 05 15 Age: 64                    │
     Name: ⓘ Heather Swinson   External ID: 1C             Measurement Mammogram [Pas         │  Factors                    852               │
     DOB: 1957/05/15           Sex: Female                 Treatment Influenza Vaccine [Pa    │  Present Factors                               │
     S.S.:                     License ID:                 Assessment Tobacco [Past Due]      │   myalgia×    sweats×    cough×                │
     Marital Status:                                       [Add] Appointments collapse        │   atypical chest pain×   smoker×               │
     User Defined:                                          No Appointments                   │   reduced tendon reflexes×                     │
     Billing Note:                                          No Recall                         │   decreased deep tendon reflexes×              │
                                                           Recurrent Appointments             │   infections×       watery diarrhea×           │
                                                            None                              │   recent travel to subtropics×                 │
[Edit] Messages expand                                     [Edit] Medical Problems co         │   season×      tobacco×                        │
[Edit] Patient Reminders expand                             Nothing Recorded                  │   tobacco use×                                 │
[Edit] Disclosures expand                                  [Edit] Allergies collapse          │   exposure to infection×                       │
[Edit] Amendments expand                                    Nothing Recorded                  │   nasal discharge×                             │
Labs collapse                                              [Edit] Medications collapse        │   recent viral illness×                        │
 No lab data documented                                     Nothing Recorded                  │   fever with cough×       viral illness×       │
Vitals collapse                                            [Edit] Immunizations collapse      │   distention×                                  │
 No vitals have been documented                             None                              │   constitutional symptoms×                     │
                                                           [Edit] Perscriptions collapse      │   pyrexia×   allergies×                        │
                                                                                              │   cough dyspnea×  infection×                   │
                                                                                              │   viral infection×  winter season× ⎫           │
                                                                                              │   fever×                           ⎬ 853       │
                                                                                              │   abnormal deep tendon reflexes×   ⎭           │
                                                                                              │   infectious diarrhea×                         │
                                                                                              │   shortness of breath×                         │
                                                                                              │  ┌──────┐    ┌──────┐    ┌──────┐              │
                                                                                              │  │ 🖥  │    │ 🖩  │    │ 🩺+ │              │
                                                                                              │  │Differential│ │Factors│  │Tests │            │
                                                                                              │  └──────┘    └──────┘    └──────┘              │
                                                                                              │     832↗        834↗       836↗                │
                                                                                              └────────────────────────────────────────────────┘
                                                                                                              ┌──────┐
                                                                                                              │ 🗙  │ ◂   501
                                                                                                              └──────┘

Example Interaction

FIG. 10F

Calendar  Flow Board  Recall Board  Messages  Patient/Client  Fees  Modules  Procedures  Administration  Reports  Miscellaneous  Popups  About   — □ ×

Patient: Heather Swinson ×
DOB: 1957 05 15 Age: 64                            ⟲ + Open Encounter None    800                       Jennifer Lee
                                                    View Past Encounters (2)▼                          Search by any ⌕

◀ Calendar ⊠ ⊟ × | Patient Finder ⊠ ⊟ × | Dashboard ⊠ ⊟ × | Past Encounters and Documents ⊠ ⊟ ×

Medical Record Dashboard – Heather Swinson     810

Dashboard History Report Documents Transactions Issues Ledger External Data

Billing
[Edit] Demographics collapse                                                    ┌─────────────────────────────────── ×
| Who | Contact | Choices | Employer | Stats | Misc | Guardian |                │ ⓘ Heather Swinson     500
                                                                                │   DOB: 1957 05 15 Age: 64
Name: ⊙ Heather Swinson          External ID: 1C                                │                            ─ 811
DOB:  1957/05/15                 Sex:        Female                             │ Factors ── 852
S.S.:                            License ID:                                    │ diminished deep tendon reflexes ×
Marital Status: ⊙                                                               │ wheeze ×
User Defined:                                                                   │ upper extremity edema ×   tired ×
Billing Note:                                                                   │ recent exposure ×   dyspnea ×
                                                                                │ ronchi ×  nonanginal chest pain ×
                                                ID Card/Photos expand           │ nonbloody diarrhea
                                                [Edit] Clinical Reminders c     │ prolonged diarrhea
[Edit] Messages expand                          Measurement Weight [Past Due]   │ breathlessness ×
[Edit] Patient Reminders expand                 Assessment Colon Cancer Scree   │ acute severe chest pain ×
[Edit] Disclosures expand                       Measurement Mammogram [Pas      │ diabetes ×
[Edit] Amendments expand                        Treatment Influenza Vaccine [Pa │ absent deep tendon reflexes ×
Labs collapse                                   Assessment Tobacco [Past Due]   │ Not Present Factors
  No lab data documented                        [Add] Appointments collapse     │ night sweats ×   edema ×
Vitals collapse                                   No Appointments               │ headache (MEN1/2) × ── 854  visual change ×
  No vitals have been documented                  No Recall                     │ recent travel ×
                                                Recurrent Appointments          │ visual changes ×
                                                  None                          │ bulls-eye-shaped rash ×
                                                [Edit] Medical Problems col     │ pneumonia ×
                                                  Nothing Recorded              │ abdominal tenderness ×   chills ×
                                                [Edit] Allergies collapse       │ hemolysis ×
                                                  Nothing Recorded              │ expiratory wheezing ×
                                                [Edit] Medications collapse     │ palpitations ×   swelling ×
                                                  Nothing Recorded              │                            ─ 855
                                                [Edit] Immunizations collapse   │  ⌬       ▦           ⚕+
                                                  None                          │ Differential  Factors     Tests
                                                [Edit] Perscriptions collapse   │   832      834  836
                                                                                │                            ⟨ ─ 501
                                                                                └───────────────────────────────────

Example Interaction
FIG. 10G

Example Interaction

Calendar  Flow Board  Recall Board  Messages  Patient/Client  Fees  Modules  Procedures  Administration  Reports  Miscellaneous  Popups  About  — ☐ ✕
Patient: Heather Swinson ✕                                                                                                               Jennifer Lee
DOB: 1957 05 15 Age: 64                                                                                          800       ↺ + Open     Search by any ◌ ◌
                                                                                                                     View Past Encounter
◄ Calendar ⌀ ⊕ ✕  Patient Finder ⌀ ⊕ ✕  Dashboard ⌀ ⊕ ✕  Past Encounters and Documents ⌀ ⊕ ✕

Medical Record Dashboard – Heather Swinson  810                                    ① Heather Swinson        ✕
                                                                                     DOB: 1957 05 15 Age: 64  ⚥⚤  894
Dashboard History Report Documents Transactions Issues Ledger E                    Differential Diagnoses
Billing                                                  Visit in progress
Edit Demographics collapse                               Present Factors  864      Idiopathic pulmonary        <10 ♂⁺
 Who | Contact | Choices | Employer | Stats | Misc | Guardian   rapid weightloss ✕   fibrosis >
         Name: ⊕ Heather Swinson  External ID: 1C         decreased body weight ✕    crackles
         DOB: 1957/05/15               Sex: Female        smoking (ischemic gangrene) ✕   clubbing
         S.S.:                         License ID:        exercise ✕  diabetes mellitus ✕   family history
         Marital Status:                                  cough ✕  weight loss of >5% ✕
         User Defined: ⊕                                  cigarette smoking ✕  fatigue ✕   Coronavirus disease 2019   <10 ♂⁺
         Billing Note:                           861      tobacco smoking ✕                  (COVID-19) >
                                                          shortness of breath ✕  smoking ✕    altered sense of taste
Edit Messages expand                                      shortness of breath with exercise ✕   altered sense of smell
Edit Patient Reminders expand                             dry cough ✕       tired ✕            fever
Edit Disclosures expand                                   weight loss ✕     weight ✕
Edit Amendments expand                                    young-onset diabetes ✕              Pulmonary tuberculosis >   <10 ♂⁺
Labs collapse                                             active smoking ✕                    fever
 No lab data documented                                   dyspnea ✕    ronchi ✕               anorexia
                                                          weight loss >10% body weight ✕       pleuritic chest pain
Vitals collapse                                           gradual weight loss ✕  smoking ✕
 No vitals have been documented                           smoking history ✕  diabetes ✕       Middle East respiratory    <10 ♂⁺
                                                          breathlessness ✕                    syndrome (MERS) >
                                                          malaise ✕             867
                                                                                              Acute exacerbation of     <10 ♂⁺
                                                         Not Present Factors                  chronic obstructive
                                                          poor sleep ✕   leg swelling ✕        pulmonary disease >
                                                          difficulty sleeping ✕  chills ✕
                                                          fever ✕       866                  Differential  Factors   Tests
                                                                                              832           834       836
                                                         Edit Prescriptions collapse
                                                                      892

Example Interaction
*FIG. 10I*

AUGMENTED INTELLIGENCE FOR NEXT-BEST-ACTION IN PATIENT CARE

This application claims priority of U.S. provisional patent application No. 63/067,774, filed Aug. 19, 2020, entitled "SYSTEM AND METHOD FOR AUTOMATED GENERATION OF NEXT-BEST-ACTION FOR PATIENT CARE," which is hereby incorporated by reference.

FIELD OF THE INVENTION

The present invention relates generally to augmented healthcare decision making for a physician or clinician across medical specialties. More specifically, the present invention relates to augmenting the clinician by helping validate or expand their consideration in-context, in real-time and during patient reviews.

BACKGROUND OF THE INVENTION

Clinicians do outstanding work, but they face astounding challenges including rapidly expanding medical knowledge humanly impossible to keep current on, high cognitive loads and limited time per patient. Many of these challenges have been summarized in the seminal 2015 publication from the National Academy of Medicine: "Improving Diagnosis in Health Care." These challenges arise from the combination of the intrinsic complexity of the practice of medicine, the complexity of healthcare delivery, and natural human decision making biases. As such they are system-level challenges.

The consequence of these system-level challenges means the health of every human is likely to be seriously impacted in their lifetime. Specifically, diagnosis is central to healthcare, yet according to the National Academy of Medicine, every human in our lifetime is likely to experience a diagnostic error. Diagnostic errors are the most common, costly and catastrophic of medical errors with a cost of $250-$500B in the U.S. alone. Further, misdiagnosis is the primary cause of serious medical errors and the estimated diagnostic error rate is 15%.

The causes of diagnostic error can generally be attributed to: the rising number and complexity of identified diseases and new diagnostic tests available (including the plethora of new primary care research); technology burdens (including the use of EHR systems as record-keeping rather than diagnostic tools, data overload and alert fatigue); the clinician cognitive process which requires thinking fast 95% of the time and eliminating any cognitive biases; and the diminishing time available for the clinician to perform an examination (limited by visit duration, documentation burdens and administrative time sinks).

Previous high-profile attempts to use artificial intelligence to automate diagnosis have been unsuccessful in large part because either artificial intelligence was applied to huge volumes of Electronic Health Record data (the majority of which contain at least one inaccuracy) or artificial intelligence was used to attempt to create clinical insight from large numbers of published medical papers, where the linkages between semantic concepts and clinical meaning is highly complex and open to interpretation. Other attempts to support diagnosis and medical decision making such as manual search clinical decision support databases have a variety of drawbacks. They are often time consuming and require the clinician to know what needs to be looked for. Searching papers directly such as from the Web site PubMed.gov, while useful for research and learning, is also time consuming to use and can be very onerous to parse through the sheer number of studies. Public search engines have a variable quality of information and their business models can mean searches are not generally suited to expert domains. Social media has privacy concerns and there can be a limit on the number of patients discussed. Clinicians may attempt to rely upon colleagues or conferences, but the use of colleagues is limited by available free time and conferences have limitations such as patient privacy, delays in decision making, etc.

Accordingly, systems and techniques are urgently desired that can augment clinical expertise to improve the accuracy and timeliness of the diagnosis of a patient condition, followed by the best appropriate treatment, in a manner whereby the clinician expert makes the decision, but they are augmented in their decision making by an invention which can solve the structural challenges described above.

SUMMARY OF THE INVENTION

To achieve the foregoing, and in accordance with the purpose of the present invention, a system is disclosed that harnesses the rapidly growing body of scientific medical knowledge in real time and in context for clinicians and their patients. The system empowers clinicians with evidence-based augmented intelligence to efficiently reach the best diagnosis followed by the most effective treatment every time, and to accelerate the world's shift to augmented healthcare.

Augmented decision making refers to the design of a human-centered partnership of people and artificial intelligence (AI) working together to enhance cognitive performance, including decision making and learning. The present invention combines experts, evidence and AI to address the structural barriers clinicians face in medical decision making. These structural barriers include: the rapidly expanding body of medical knowledge for which it is now humanly impossible to keep current on and apply; the expanding field of high definition medicine including -omics; the thousands of potential diagnoses; the extensive array of diagnostic tests; complex drug-drug, drug-food, drug-supplement, drug-disease interactions; complex treatment options especially where a patient has more than one medical condition; natural human biases; limited time available per patient encounter; and heavy cognitive loads. More specifically, the present invention relates to augmenting the clinician by helping validate or expand their consideration in-context, in real-time and during patient reviews. Specifically, the present invention extracts pertinent findings or "signals" from unstructured and structured data from prior encounters, combines these with real-time in-encounter data, to create a list of: 1. suggested differential diagnoses based on the patient context and evidence-based medicine; 2. next-best-actions for both history taking and examination to help narrow down potential differentials; 3. next-best-actions for diagnostic testing; and 4. next-best-actions for treatment.

The inventors believe that combining clinician experts with the ever-expanding body of evidence-based medical science is not only an imperative given the challenges healthcare faces today, but will lead to a new level of sustained and continuously improving human health betterment.

Note that the terms "differential diagnosis," "diagnosis" and "condition" are used interchangeably and for the purpose of the invention refer to "differential diagnosis." A differential diagnosis is a method of analysis of a patient's history and physical examination to arrive at the correct diagnosis. It involves distinguishing a particular disease or condition from others that present with similar clinical features. All terms relating to the probability of a condition, diagnosis or differential diagnosis, for the purpose of the invention, refer to the system's strength of match of all extracted information for a patient (which include the clinician expert actions) to the system's knowledge base, and do not relate to the absolute probability a patient has of a particular differential diagnosis or condition.

Instead of applying artificial intelligence to attempt to create clinical insight from enormous databases of unstructured and structured data that are known to contain both inaccuracies and highly complex semantic concepts and linkages between those concepts, the present invention applies artificial intelligence to smaller, organized, structured databases, curated by human experts, in order to obtain results. This superstructure of expert human data is then enriched by real-world data (RWD) in the context of the expert-curated core.

Specifically, the invention makes use of rigorously curated, evidence based-medicine data, where factors relating to diagnosis and treatment are clearly defined and further have been ranked by clinical importance based on the available evidence and clinical experience. The invention's design to make use of such rigorously curated data means that the data the AI is applied to is both referenceable and adheres to a recognized standard for expert evidence curation.

The invention is then able to distinguish between "extracting" and "matching" concepts. The invention may include a "problem finding" framework whereby: 1. the evidence-based concepts are defined by the underlying curated data in order to inform the extraction from clinical charts and other data, and 2. once extractions have been made, they can be matched to these evidence-based medicine concepts.

The invention may make use of multiple additional databases building off the evidence-based core, and enriches the core itself, by: 1. making evidence-based diagnostic factors tractable for machine processing such as structuring factors into discrete concepts; 2. connecting evidence-based medicine to structured corpora such as SNOMED-CT and LOINC; 3. enriching with further data including but not limited to Adverse Drug Reactions, Rare Diseases, medical abbreviations and patient-described symptoms. Thus, the knowledge base is augmented and structured specifically to allow the models of the information extraction engine to produce more accurate results.

Embodiments of the invention provide evidence-based, explainable diagnosis and next-best-action suggestions in real-time, taking data from the clinical chart, patient encounter, and test results to augment the clinician. We empower clinicians across specialties with augmented insights. We solve increasingly critical cognitive challenges at the front-end of healthcare, by increasing efficiency in decision making, reducing resource wastage, and improving both patient outcomes and physician experience.

The invention benefits patients, physicians, clinicians, healthcare systems and payers. Patients receive the best possible health outcome in the most timely fashion and benefit directly today and throughout their lives as the clinicians that treat them are empowered by the growing body of scientific evidence and the advances this provides. This care goes beyond what artificial intelligence or clinicians could achieve alone, with the clinician leading the decision making at every step. A clinician empowered with the invention is practicing cutting-edge care built on up-to-the-moment research, shortening knowledge transfer from "bench to bedside" to near real time. Regarding healthcare systems, the invention: improves patient outcomes, reduces physician burnout, increases efficiency, increases coding confidence, and reduces avoidable re-admitting of patients. For payers, the invention: improves patient outcomes, improves quality of care, improves accuracy of actuarial analysis, reduces avoidable resource wastage, and reduces capitation costs.

The system brings evidence-based medicine in context in real time into clinical workflow, to augment—not replace—the clinician, helping the clinician validate or expand their considerations at every key decision point. The instrumentation is automatically populated with data from an EHR system pre-encounter as well as with real-time data during patient-physician encounters. Using the extracted clinical information, the system dispassionately presents the most likely differential diagnoses, effectively eliminating both confirmation bias and the errors of not knowing what one does not know. The platform is useful for a broad range of specialties including primary care, telemedicine, medicine subspecialties and is useful for clinicians of varying levels of experience.

In a first embodiment a computer model extracts clinical diagnostic factors from electronic text from an EHR system for a particular patient. These factors are matched against sets of ranked diagnostic factors, each set associated with the condition, to produce a list of probable conditions, the probabilities of which are based on the strength of the matches of the extractions with the system's knowledge base. For each condition, the method determines unknown diagnostic factors that are not known to be present or absent in said patient, then displays these unknown diagnostic factors ordered by the probability that each one indicates its associated condition.

These factors comprise the next-best-actions including: history taking, examination, and diagnostic tests. The system displays extracted and matched factors, and the connections between them and probable conditions. The system responds in real-time to clinician action through various mechanisms, including: clinician and patient-transcribed conversation; clinician updating the chart; clinician clicking on a next-best-action response from the patient; clinician clicking on a next-best-action to, e.g., to order a diagnostic test; and the clinician running "what-if" scenarios (including but not limited to: 1. entering a differential diagnosis of interest whereby the system shows supporting and detracting findings for that; and 2. adding or removing the finding).

In a second embodiment a computer model extracts performed treatments and clinical diagnostic factors from electronic text from an EHR system for a particular patient. These factors are matched against sets of ranked diagnostic factors, each set associated with the condition, to produce a list of probable conditions. The probabilities of which are based on the strength of the matches of the extractions with the system's knowledge base. For each condition, the method determines a list of unperformed treatments that have not been performed for said patient, and then displays these unperformed treatments. The system is able to suggest treatments for either a single condition or where a patient has more than one condition (comorbidity).

In a third embodiment a computer model extracts clinical diagnostic factors from electronic text received from a speech recognition module that has transcribed a conversation between a clinician and a patient. These factors are matched against sets of ranked diagnostic factors, each set associated with the condition, to produce a list of probable conditions. The probabilities of which are based on the strength of the matches of the extractions with the system's knowledge base. For each condition, the method determines unknown diagnostic factors that are not known to be present or absent in said patient, then displays these unknown diagnostic factors ordered by the probability that each one indicates its associated condition. The system works in real time to provide insights back to the clinician as the conversation progresses with the patient.

In a fourth embodiment a computer model extracts performed treatments and clinical diagnostic factors from electronic text received from a speech recognition module that has transcribed a conversation between a clinician and a patient. These factors are matched against sets of ranked diagnostic factors, each set associated with the condition, to produce a list of probable conditions. The probabilities of which are based on the strength of the matches of the extractions with the system's knowledge base. For each condition, the method determines a list of unperformed treatments that have not been performed for said patient, and then displays these unperformed treatments. The system is able to suggest treatments for either a single condition or where a patient has more than one condition (comorbidity). The system works in real time to provide insights back to the clinician as the conversation progresses with the patient.

BRIEF DESCRIPTION OF THE DRAWINGS

The invention, together with further advantages thereof, may best be understood by reference to the following descriptions taken in conjunction with the accompanying drawings in which:

FIG. 4 illustrates an example database with treatments ranked for a condition.

FIG. 5 illustrates the addition of a clinical note.

FIG. 9A is a particular condition and below are the key diagnostic factors, followed by other diagnostic factors and finally by weak diagnostic factors.

FIG. 9B is the same condition and below are the first investigations to order, followed by other investigations to consider.

FIG. 10A illustrates the beginning of the example interaction in which a clinician has opened an EHR system which displays its user interface having a patient finder tab showing any number of patients whose medical records may be opened.

FIG. 10B illustrates the example interaction after the clinician has opened the diagnostic glass user interface.

FIG. 10C illustrates the example interaction after a patient has been selected and her context has been loaded.

FIG. 10D illustrates the example interaction after the clinician has selected a particular diagnosis.

FIG. 10E illustrates the example interaction after the clinician has selected the beaker icon, in order to view the laboratory tests, examinations and investigations which are also next best actions.

FIGS. 10F-G illustrate the example interaction after the clinician has clicked upon the factors icon and has scrolled farther down the window.

FIG. 10I illustrates the example interaction after the clinician has activated the transcription software and microphone and has scrolled farther down the window.

DETAILED DESCRIPTION OF THE INVENTION

System Overview—Off-Line Training and Processes

Figure 1:
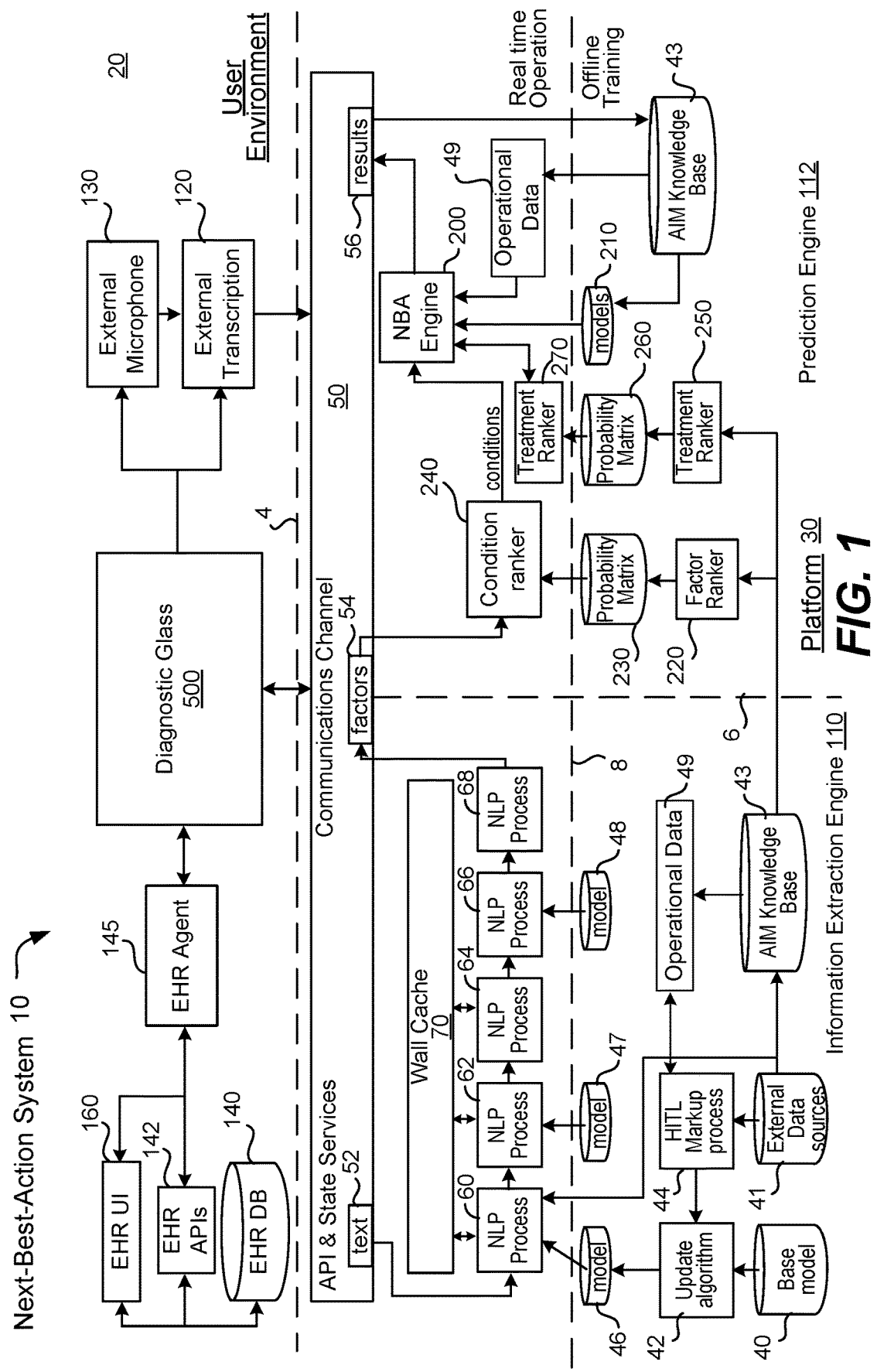
FIG. 1 illustrates a next-best-action system able to augment the differential diagnoses of a patient condition and to present pertinent findings, probable differential diagnoses based on the strength of match of extracted findings with the knowledge base, and next best action suggestions for that patient.

FIG. 1 illustrates a next-best-action system 10 able to evaluate a patient's condition and to present possible conditions, probabilities and next best actions for that patient. Generally, system 10 may be viewed as having a user environment 20 and a system platform 30, shown separated by horizontal dashed line 4. User environment 20 is that hardware and software generally located on customer premises (such as in hospital, clinic, doctor's office, etc.), while system platform 30 is generally that hardware and software located at offices and locations owned by or under order control of the provider of system 10, such as locations controlled by Recovery Exploration Technologies, Inc. Nevertheless, certain components of user environment 20 such as the EHR database 140 may be located remotely from the physician (e.g., in the cloud) and in one embodiment the diagnostic glass application 500 is Internet cloud based and accessed by a physician using a Web browser on a computer in his or her office. Components of system platform 30 may also be cloud based. Communications channel 50 is a software layer that communicates information between diagnostic glass 500 of the user environment 20 with various components of the system platform 30 and includes application programming interfaces (APIs) such as voice start, voice end, live note, historical note, patient context, prediction set, user action, etc., and also includes state services such as user context, conditions, factors, factor statuses, probabilities, and actions. Note that "clinician" used herein refers to medical doctors, physicians, physician assistants, nurse practitioners and other medical professionals qualified to diagnose, treat and care for patients.

Components of system platform 30 can be further divided by vertical dashed line 6 into an information extraction engine 110 that extracts diagnostic factors 54 from verbatim text 52 (from an EHR record or from a transcribed conversation) and a prediction engine 112 that takes these diagnostic factors and produces results 56 in diagnostic glass 500 for the physician such as conditions, probabilities and next best actions. Components of both the information extraction engine 110 and the prediction engine 112 can yet be further divided by horizontal dashed line 8 into those components and processes that are used or occur off-line (i.e., before the clinician begins using diagnostic glass 500 in order to produce a next best action) either for training or for preparation for online use, and those components and processes that are used or occur during real-time operation of system 10. How and when each component is used and when a process occurs will be made clear in the below explanation.

Beginning with the off-line aspect of information extraction engine 110, engine 110 is used to build and train models 46-48 of which there may be any number (some NLP processes 60-68 use a model and some do not). Base model 40 is a pre-trained model used to understand the semantic context of text entities and is typically a model such as BERT; it is used as the base for models 46-48. To begin with, any number and type of external data sources 41 may be used to develop models 46-48 that will be used during real-time operation to extract the relevant diagnostic factors 54 from verbatim text 52. External data sources 41 may include: BMJ (British Medical Journal) databases, content on rare diseases, SNOMED-CT (Systemized Nomenclature of Medicine—Clinical Terms), investigation LOINC (Logical Observation Identifiers, Names, and Codes) codes, laboratory test reference ranges, drug interactions (drug-drug, drug-condition, drug-food), clinical dictionaries, and CPT (Current Procedural Terminology) codes. In addition, evidence-based medicine sources are used and include a collection of external data, such as datasets of clinical support reference content for healthcare professionals which contain best practices, evidence-based research relevant for clinical decision support including diagnosis, prognosis and treatment. These datasets are continuously updated with emerging evidence.

These external data sources are refined, enriched and combined into the system's knowledge base, known as the Augmented Intelligence in Medicine Knowledge Base, or AIM-KB 43. In addition to external data sources 41, AIM-KB 43 contains Real-World Data (RWD) and Real-World Evidence (RWE) captured and analyzed in a manner compliant with applicable regulation and used to both evolve AIM-KB data and associated models by both human expert and machine learning means. RWD and RWE means internal data captured and derived from real world use of the invention, and any analysis and insights generated from de-identified RWD, including data from patients and users.

AIM-KB 43 comprises refined, enriched and linked data from external data sources. The enrichment includes enabling evidence-based medicine to be useful for machine processing, including but not limited to XDFs and XDIs (Cross-Condition Diagnostic Factors and Cross-Condition Diagnostic Investigations). An XDF is a Cross-Condition Diagnostic Factor, a clinical factor that may be evident in a number of conditions. Evidence-based medicine tends to consider diagnostic factors on a condition by condition basis. XDFs enable these factors to be disambiguated across conditions by the system and in the cases where the same factor applies to multiple conditions, but may be referred to by different terminology, to enable those like factors to be understood as having the same meaning. By way of example, the XDF, confusion 442 can be seen to be related to conditions Amphetamine overdose 420, Ischemic stroke 422, and Meningococcal disease 423. In a similar vein, XDIs, Cross Diagnostic Investigations, refer similarly to investigational tests that are the same but may be referred to with different nomenclature when associated with different conditions, or when referred to by different clinicians during the course of their documentation, e.g. "Ph", "PO4", "Phos", and "Phosphorus, serum" all refer to the same blood test for the amount of the element phosphorus in a person's blood.

Further, AIM-KB 43 may be enriched by the capture and use of real world data (RWD) and real world evidence (RWE) for system 10 use, including but not limited to ethically-captured and prior-agreed, de-identified data relating to clinician actions, patient charts, and closed-loop feedback outputs. And, the RWE is captured with reference to the underpinning EBM superstructure. The AIM-KB combines machine-processable EBM, further enrichments and RWE. The AIM-KB may be implemented as a knowledge graph.

The AIM-KB thus enables a virtuous circle of enhancing expertise: we know evidence-based medicine (EBM) is the best starting point today to support experts in their determinations based on the context of the patient, but we also know it has gaps and biases. AIM-KB is designed to enrich today's EBM with real-world evidence, addressing biases and gaps, and enabling further targeted research to be undertaken. Data in AIM-KB 43 used operationally by models in Information Extraction Engine 110 and Prediction Engine 112 is stored in and processed by Operational Data 49. Such data is used for including but not limited to: matching by models in Information Extraction 110 and next best actions in Prediction Engine 112.

In addition to the above external data sources, database 49 may also include optional diagnostic and other clinically relevant data (such as a response to a medication) not yet in EHR system 140, which the clinician deems to be of potential relevance to the diagnostic or clinical process, including but not limited to real-time patient device data (e.g., heart rate, heart rate variability, step count and medical device physiological data) and generated data (e.g., how a patient is feeling). Such data comes from an increasing number of sources including patient applications, patient consumer devices, medically provided IoMT devices and emerging diagnostic technologies.

In block 44, information in the external data sources 41 is reviewed via an HITL (human in the loop) markup process which involves trained clinicians examining the output of the running models and indicating whether the model correctly identified the factors. In the instances when the model does not correctly identify the clinically correct information, the clinicians provide a variety of feedback that is used to retrain the models. This feedback may come in a number of forms including but not limited to the selection of alternative matches (factor matching), and the indication that the text either supports, contradicts or does not provide enough evidence to support the selection (entailment), for example. The base model 40 is then combined with the block 44 output and via an update algorithm 42 is used to produce any of models 46-48. Preferably, each model has its own form of HITL and update algorithm. The 40/42/44/46 block may be effectively repeated for each different model (although in practice some can use the same training information). Once models 46-48 have been produced offline and further trained, they are then ready for use by the various NLP process modules 60-68 during real-time operation. Note that while the diagram shows NLP processes 60, 62, 64, 66, and 68, the intention is not that there are exactly five NLP processes but rather a pipeline of one or more, each of which may be driven by a unique model.

Preferably, all component blocks of the invention operate as autonomous micro services with distinct APIs. This means, for example, that the API and State Services 50, Information Extraction Engine 110, and Prediction Engine 112 can process inputs from multiple product embodiments of the invention utilizing these shared components for multiple use cases. For example, the Diagnostic Glass User Interface 500 is used by clinicians in real time in workflow. In another embodiment, the invention may be used by clinicians for electronic consults where the patient is not present in the encounter.

Also included is a factor ranker module 220 which constructs off-line factor probability matrix 230. Factor ranker 220 uses a diagnostic factor ranking algorithm that ranks diagnostic factors in order of the most relevant factors for diagnosing a specific condition, including but not limited to traditional diagnostic factors such as: gender, age, signs, symptoms, family history, medications, -omics (structural and/or functional indications). In addition to traditional diagnostic factors being ranked for a particular condition, factor ranker 220 will also include and rank the results of laboratory tests and examinations (also referred to as investigations) which may include fluid (e.g. blood, urine, semen, and CSF) analysis, diagnostic imaging (CT, MR, X-ray, PET, ultrasound, endoscopy), and pathology analysis among others. For purposes of the factor ranker 220, all of these traditional diagnostic factors, laboratory tests, examinations and investigations are referred to as "diagnostic factors" or simply as "factors." As shown in the example given below, factor ranker 220 ranks not simply the name of the diagnostic factor per condition, but the name of the diagnostic factor along with a value. By way of example, diagnostic factors include: "gender is male," "patient has a headache," "patient skin appears yellow," "family has a history of colon cancer," "CBC blood test shows reduced hemoglobin level," "patient reflexes appear normal," "MRI of the pelvis appears normal." Thus, the value of a particular diagnostic factor (or its result, if the factor is a blood test or investigation, for example) may be a simple yes or no, a numerical value, a numerical range, the presence or absence of the diagnostic factor, an observation (e.g., "appears normal"), or other results such as a specific physiological description like "the nasopharynx is symmetric."

Figure 10C:
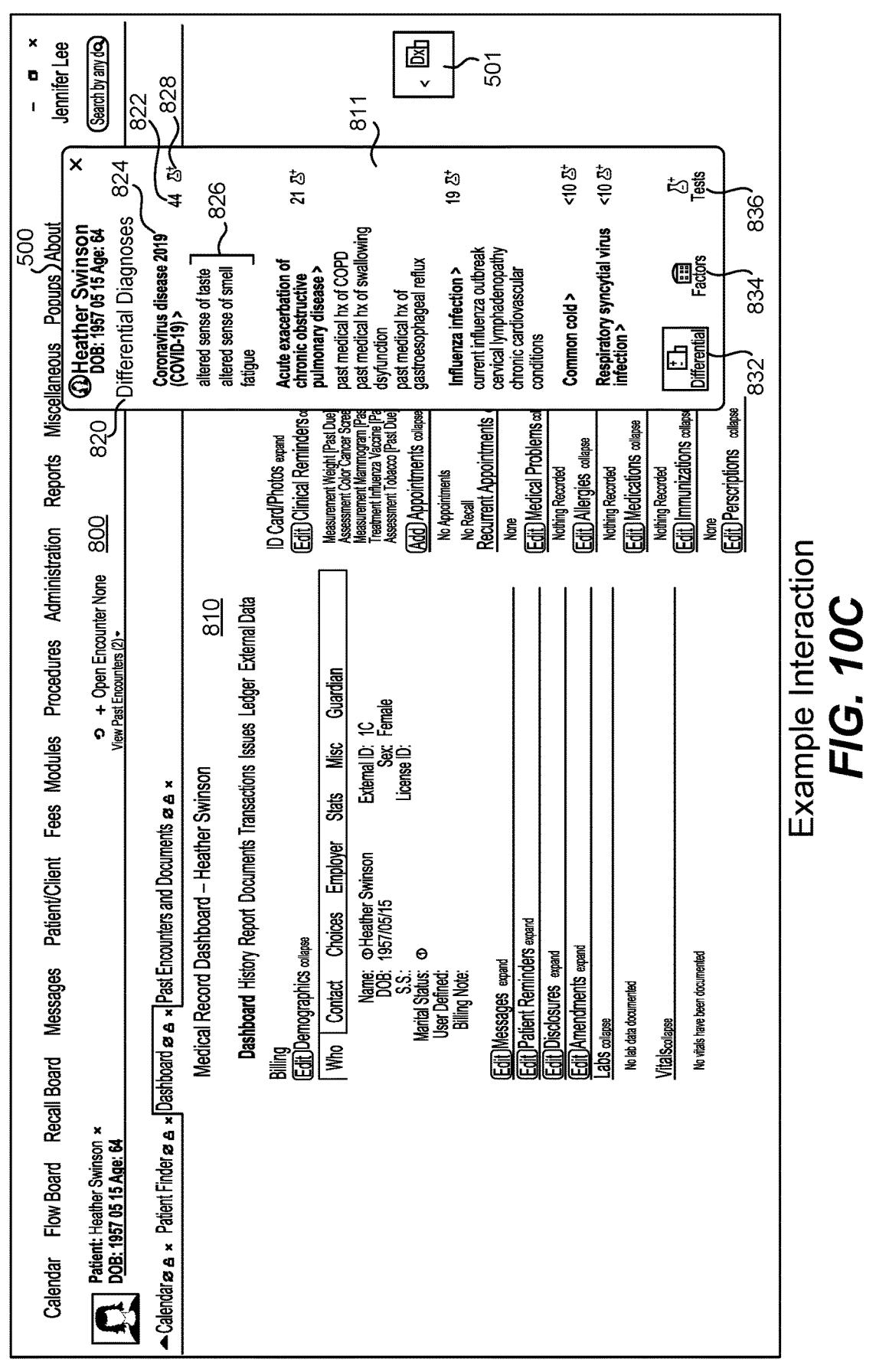

In one particular embodiment, the flow diagrams distinguish between clinical factors (such as "patient has a headache") and tests (such as a blood panel or an MRI), and the diagnostic glass shows next-best-action clinical factors and next-best-action tests separately, e.g., as in FIG. 10C at 834 and 836. In order to distinguish, when the NLP pipeline 60-68 extracts an entity (factor), that entity is marked with its type in the context of the text that it is extracted from, e.g., "clinical factor" or "test." Other types, flags, or markings per entity are also possible. All of these types flow through the system after being extracted, and in this way the UI 500 can display the different entities as desired, grouped separately, grouped together, etc. Thus, system 10 distinguishes between these two sets of factors, flags them as they are processed through the system, and can display them separately.

In general, the system distinguishes between clinical factors and tests (including examinations and investigations). For example, "a clinical factor is a factor that the physician can observe, detect quickly or have the patient describe to him," while "a test is a laboratory test, an investigation or an examination performed by the physician that is more sophisticated and takes more time." Typically, tests mostly require either the collection and processing of some sort of biological sample or a physiological analysis using some sort of device. And, while the clinical factors and tests are all lumped together in the factor probability matrix 230, in other embodiments they may be kept in separate databases or matrices. Further, while in the described embodiment the output next-best-action clinical factors are ranked against one another while the output next-best-action tests are similarly only ranked against themselves, in other embodiments both may be ranked against one another, e.g., the first next best action may be an unknown clinical factor while the second next best action may be a recommended test.

Using input from external data sources 41 (which contain thousands upon thousands of sets of diagnostic factors that each indicate a particular condition, and includes Evidence-Based Medicine knowledge with relative importance for a given factor determined by human expert), as well as the potential to combine with Real-World Data captured in the AIM-KB 43 for a given condition, a probability value is assigned via the ranking algorithm to each factor based on its relative association with that condition. In other words, a higher probability value for a factor of a condition means that this factor is more indicative of this condition than of a condition with a lower probability value for that factor.

The relative probability value for each factor for each condition is calculated as follows:

$$FR_{fc} = r(E_{fc}, L_{fc}, R_{fc}),$$

where "r" is a function that combines values associated with each factor in relationship to each condition to a single aggregate number used in the probability matrix; the function may combine values in different manners.

Conceptually, $FR_{fc}$ is a probability matrix 230 of size [f, c], where the probability value of a cell in the matrix for a diagnostic factor (f) is the relative weighting of diagnostic factor (f) relevance between 0 and 1 for a given condition (c) expressed as a function of the weightings E, L and R. $FR_{fc}$ is calculated from one or more of the components E, L, and R, with the function r being used to create a single combined ranking where more than one component for the factor is input. In many instances L or R may be null, however, when they are not they need to be combined with E in a logically consistent way.

E, L and R are defined as:

$E_{fc}$=evidence-based factor from 100% to 0% based on expert-ranked evidence-based medicine, such as from one or more evidence bases, e.g., BMJ Best Practice.

$L_{fc}$=localized factor from 100% to 0%, based on probability distributions from multiple sources, including customer EHRs. In general, given that there is an overall population distribution, these are the local variances derived by examining the data from the local EHR.

$R_{fc}$=RWD factor from 100% to 0% based on probability distributions from the sum of Real World Data and Real World Evidence in the AIM-KB 43.

Figure 6:
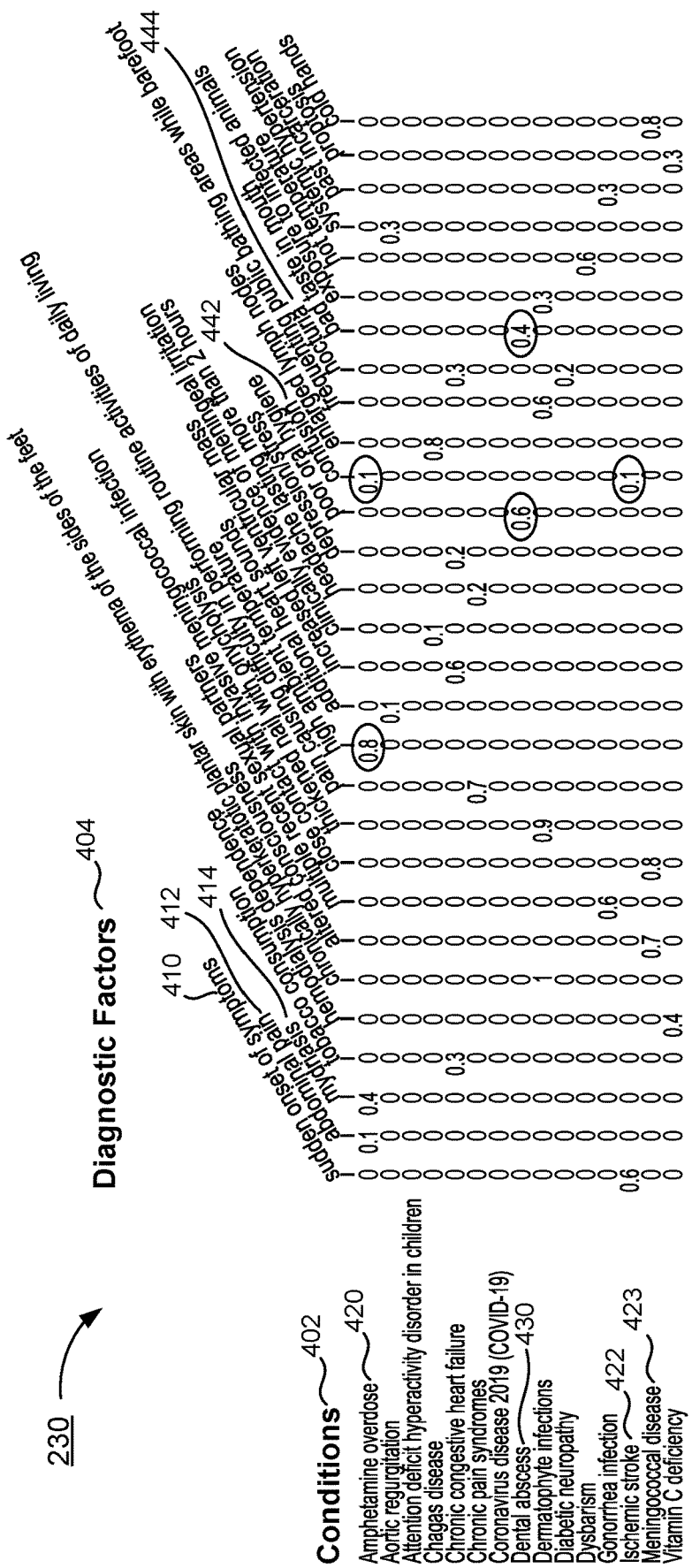
FIG. 6 illustrates a simplistic example of a factor probability matrix.

FIG. 6 illustrates a simplistic example of a factor probability matrix 230. As shown, matrix 230 includes rows of any number of conditions 402 and columns of any number of diagnostic factors 404. Shown in each cell indexed by a particular condition with a particular diagnostic factor is a probability value indicating the relative weighting a factor has for a given condition. By way of example, looking at condition "dental abscess" 430, the diagnostic factor "poor oral hygiene" has a value of 0.6. Consider a condition "hospital-acquired pneumonia" (not shown) which where the factor "poor oral hygiene" may have a score of 0.27. These values are interpreted to mean that if a patient has poor oral hygiene, this is more suggestive of a dental abscess than it is of "hospital-acquired pneumonia." Note also that diagnostic factors such as "confusion" 442 and "nocturia" 444 each may indicate different conditions if present. It should be noted the probability matrix does not define the probability of a condition given a factor or set of factors, rather, it provides the set of weights used for the strength of match of a set of pertinent positive and negative factors across conditions.

During real-time operation the condition ranker 240 will use factors 54 and the probability matrix 230 in order to rank likely conditions that the patient has. Considering another example, then, assume that the patient presents with only the three diagnostic factors 410, 412 and 414. Assuming also that a very simplistic addition algorithm is used to combine the probability values for each factor (i.e., simply add the values), the condition amphetamine overdose 420 will have a value of 0.5 and the condition ischemic stroke 422 will have a value of 0.6 based upon these three diagnostic factors. Accordingly, condition ranker 240 will rank ischemic stroke as the most likely condition with the amphetamine overdose being in second position.

As mentioned before, even though the example of FIG. 6 only shows traditional clinical factors that a clinician may elicit from a patient during examination or from his or her medical record, diagnostic factors 404 may also include results of laboratory tests (e.g., blood work), assessments (e.g., what is the patient's mental state), and the results of more sophisticated, time-consuming and expensive investigations such as MRIs, CT scans, etc. Further, even though conditions are shown in rows and factors in columns, the data may be represented the other way around, and in fact, any suitable data structure may be used to associate a probability value of a factor with a condition and not necessarily require a matrix as shown.

Treatment ranker 250 uses the same concept as factor ranker 220 to apply rankings to treatments for next-best-action engine training (including but not limited to sensitivity and specificity rankings of treatments per conditions) as well as for real-time operation. Thus, treatment ranker 250 includes a treatment ranking algorithm that produces a treatment probability matrix 260 $TR_{tc}$ that ranks treatments in order of treatments that should be tried. Generally, there may be a cost function associated with how these are selected. By way of example, consider the condition sciatica. A treatment course may be the following in this order: use of NSAIDs to reduce swelling, addition of Gabapentin to reduce nerve response, physical therapy, steroidal spinal injections, lumbar laminectomy and/or discectomy to reduce nerve compression. The last of these treatments tends to be the most effective treatment but comes at the highest cost in terms of dollars, pain, time lost from work, etc. Thus, the cost function may be based on a single measure such as dollars, pain, or time lost from work, or may be a combination of measures.

For a given condition, a probability value is assigned via the treatment ranking algorithm to each treatment based on its relative desirability at treating that condition. The algorithm uses data from external data sources 41 and AIM KB 43 which for a given condition, will typically list in order the various treatments that may be used.

The relative probability value for each treatment for each condition may be calculated in different manners. Conceptually, $TR_{tc}$ is a probability matrix 260 of size [t, c], where the probability value of a cell in the matrix for a treatment (t) is the relative weighting of treatment (t) relevance between 0 and 1 for a given condition (c) expressed as a probability of the treatment having a lower cost at treating the condition, P(f|c). $TR_{tc}$ is calculated from the evidence based medicine (EBM), and similar to the above, we can also use local variations in usage and real world data in the calculation.

Although not shown, treatment probability matrix 260 may appear similar to factor probability matrix 230 as shown in FIG. 6, having any number of rows with conditions, but instead of having columns of diagnostic factors, the treatment probability matrix includes columns of treatments. Thus, for a given condition there are any number of treatments listed, each with a probability value, and they may be listed in order of least cost to highest cost.

System Overview—Real-Time Operation

Turning now to the explanation of the real-time operation of next-best-action system 10, we will explain user environment 20 as well as those components of system platform 30 above horizontal dashed line 8 or those used during real-time operation.

EHR system of record 140 is an external database providing the EHR-stored medical data related to the patient and the diagnostic process, including but not limited to patient demographics, symptoms, investigations, examinations, laboratory test results, signs, diagnoses, treatments ordered, response to treatments and history. Data is accessed in both real time and asynchronously pre-encounter. Data is accessed via various methods including but not limited to FHIR standards. EHR Agent 145 is an event detector that automatically detects any new relevant data, including but not limited to new data added to EHR system 140 (for example, a new patient record or state change of patient data such as diagnostic data both in real-time and asynchronous modes of operation), and provides that data to diagnostic glass 500, i.e., data that is typically added by a clinician.

EHR UI 160 is the user interface of the EHR system, typically but not limited to an EHR, with diagnostic glass 500 capable of being launched from that EHR UI 160 environment with a single sign-on authorization including but not limited to SMART on FHIR (Fast Healthcare Interoperability Resources) and other relevant standards. EHR APIs 142 is a collection of APIs such as FHIR, USCDI (United States Core Data for Interoperability), CDS Hooks, and vendor specific APIs which allow EHR agent 145, user interface 160 and other components to communicate with EHR system 140.

Transcription Software 120 is any suitable third-party software for real-time speech recognition and voice transcription of the patient-clinician encounter such as the product AWS Transcribe Medical. Software 120 is also multi-lingual. External Microphone 130 is any suitable external microphone for real-time capture of relevant voice conversations of both patient and clinician for diagnostic purposes, including a patient-clinician encounter, for example both in person and via telephone, computer, etc., when the patient is remote.

Diagnostic glass 500 is a real-time, fully automated, possibly hands-free clinician application and user interface, designed specifically to be the system of interaction to effectively enable the diagnostic inquiry and exploration process. Diagnostic glass 500 is an augmented intelligence user interface to assist the diagnostic process at every step. Diagnostic glass 500 can be used in an overlay form or as a window tab. The Diagnostic glass 500 is an interface to the information extraction engine 110 as well as to the prediction engine 112 which run in parallel with the clinician's actions and do not require any additional input from the clinician.

Diagnostic glass 500 may use speech recognition technology as well as live note capture technology to collect real-time, pertinent patient encounter information and to extract pertinent positive and negative history from the EHR medical chart. This verbatim text (either from speech recognition, live notes or from the EHR system) is then converted in real time into factors 54 by the information extraction engine 110 for use by the prediction engine 112.

Diagnostic glass is automatically pre-populated from the EHR system 140 pre-encounter. The glass can either be pre-populated pre-encounter or as soon as the current patient context is established by the clinician selecting a patient in the EHR. With this data, prediction engine 112 may show the top five (or other number) differential diagnoses (conditions) with probabilities, the top five (or other number) next best actions, and suggested history and examination queries. These suggestions are continuously updated throughout the visit based on newly available visit information. The clinician can also use "one-click ordering" of tests via the diagnostic glass to create further efficiencies downstream. For the clinician, diagnostic glass 500 helps bridge specialty knowledge and acts as a safety net to prevent diagnostic error. Symptoms, signs or conditions that may seem unrelated will be incorporated into a unifying diagnosis.

Diagnostic glass 500 may be updated in real-time via voice transcript (from speech recognition), clinician entries or selections, and live note entry. The diagnostic glass 500 also has a manual data entry feature. In one embodiment, diagnostic glass 500 is an application integrated into the EHR/EMR environment via relevant standards such as a SMART (Substitutable Medical Applications, Reusable Technologies) on FHIR application for EHRs (such as Epic and Cerner), and is integrated into the clinical workflow. In another embodiment, Glass 500 is a standalone system, integrated with relevant external data sources. Another embodiment is a specifically designed physical device, including but not limited to a physical glass-like form with augmented reality, dedicated to the purposes of diagnostic inquiry.

Diagnostic glass 500 can instigate external voice capture via microphone 130 and transcription 120. Diagnostic glass also has an automatic feature to provide insights to a clinician where there is a high probability that a next best action should be considered where it has not already been done so. All highlights and suggestions are provided for expert consideration and not as a replacement for the clinician. Thus, the diagnostic glass 500 provides real-time, in-context differential diagnosis and next-best-action suggestions to validate and expand clinical consideration.

Turning now to the real-time operation of system platform 30, information extraction engine 110 takes as input 52 (both in real time and asynchronously) unstructured and structured data (from any external source, including EHR medical records), clinician-patient transcripts and patient medical or consumer devices with health data. The engine 110 uses multiple techniques including NLP (natural language processing), NER (named entity recognition), NEL (named entity linking) and semantic search architectures to: 1. identify entities, attributes, relationships, and phrases of interest in the medical record, clinician notes and patient-clinician oral conversation and 2. match this identified information in the corpus of knowledge from AIM-KB 43 in order to make conclusions 54 as to the presence or absence of diagnostic factors, a value of a diagnostic factor, a range for a diagnostic factor, an opinion as to a diagnostic factor, etc. Thus, results from scanning an EHR record (for example) can result in one of three states for a factor: 1) pertinent positive—it is documented as occurring, 2) pertinent negative—it is documented as not occurring, or 3) unknown—it is not documented as either occurring or not occurring. The engine 110 operates in both real-time (during a patient encounter) and asynchronously (pre encounter and in-between patient encounters) and is also multilingual.

During real-time operation, verbatim text 52 is received at communications channel 50 via diagnostic glass 500 and may have originated from an initial reading of the patient medical record in EHR system 140, from notes that have been typed into the patient medical record by a clinician during an encounter, or from a transcription of a conversation between the clinician and the patient. Because this text is in raw form, a pipeline of NLP (natural language processing) processes 60-68 (along with any models 46-48 that each may use) are used to extract the pertinent diagnostic factors 54 for input into the condition ranker 240. There may be any number of NLP processes, each may use a model or not, and each may choose to store information in the wall cache 70. Wall cache 70 is a temporary memory storage location that each NLP process may use to store intermediate results, may store the original verbatim text, may store its final results, or may store nothing. Each NLP process may in turn use information stored in wall cache 70. The NLP processes that may be used include but are not limited to: Word Segmenter, Sentence Segmenter, Negation Cues, Negation Scopes, NER (Named Entity Recognition), Relationship Prediction, NEL (Named Entity Linking), Phrase Extractor, Composite Matcher, Embedding Matcher, Graph Matcher, NLI and Long-to-Long Matcher. As mentioned above, the factors 54 derived from text 52 in this manner are, for example, a factor having a particular status or value (e.g., "patient has a headache"), the result of an examination (e.g., "systolic blood pressure is over 140"), the result of a laboratory test (e.g., "white blood cell count is below a minimum"), the result of a particular more sophisticated investigation (e.g., "brain scan shows a tumor"), etc.

For real-time operation, prediction engine 112 includes a condition ranker 240, a treatment ranker 270 as well as the next-best-action engine 200. Condition ranker 240 is a computer model developed using the BMJ Best Practices evidence base and other data sources as relevant, which provides a top N list of the most probable conditions or condition sets (disease states) a patient may have given the current state of data, including but not limited to factors 54 and prior actions. Prior actions include tests that have been performed or diagnostic questions that have been asked to determine the status of factors. Essentially, condition ranker 240 matches the patient's factors 54 with the diagnostic factors found in the factor probability matrix 230 in order to output the list of the most probable conditions. One embodiment of the condition ranker 240 uses Bayesian algorithms Another embodiment of the condition ranker is based on a global and local consistency score using combinatorial Hodge Theory techniques for ranking, alongside techniques for structured domain knowledge extracted from the BMJ Best Practices and other data sources as relevant.

The condition ranker provides clinicians with a sense of how confident the system is in the ranking of the various conditions at each step of the diagnostic process, as well as the reason for each condition being on the list. This confidence represents the strength of match of found factors to conditions in AIM-KB, the confidence being a function of the values in the probability matrix.

Similar to the condition ranker, treatment ranker 270 uses its treatment probability matrix 260 in order to output the next best treatments for a particular condition. As the top conditions were determined by condition ranker 240 and then passed to the next-best-action engine 200, engine 200 may query treatment ranker 270 with a particular condition and in return receive a list of treatments for that condition ranked as has been discussed above.

Prediction engine 112 takes as its input a State S1 representing the set of factors 54 at a point in time for a particular patient, including but not limited to: patient demographics, symptoms, signs, prior history, examinations, laboratory tests, investigations run, results, assessments, treatments, responses to treatments, existing conditions and other prior clinical actions and relevant data. The prediction engine 112 outputs for a given State S1 a set of clinically relevant next best actions A1 (results 56) to support clinical outcomes including: the diagnostic process, treatment process and surveillance process, including the top N most probable diagnoses (conditions) for the clinician to consider and next best actions across history taking, diagnostic tests and medications.

This next-best-action set A1 can be extended to the top N (e.g., top ten, top twenty, and so on). With each clinician action that changes the input state set of data from S1 to S2 (such as asking the patient a question in an encounter, performing an examination, running a test, returning for assessment after a medication, etc.) the prediction engine 112 provides a set of updated next best actions A2 in real time. The prediction engine augments the clinician to help validate or expand clinical thinking and action at every step of information interaction with the patient, and helps ensure the clinician is sighted on the most clinically relevant next-best set of actions to consider at any given point in time given the known information state of a patient and available scientific evidence. The prediction engine provides relevant actions for both single disease states and for comorbidities. Next best actions continue to be automatically provided based on any relevant information state change, including both new data on patient state or iterations through training. The prediction engine 112 automatically provides closed-loop feedback to the clinician at each step. Actions are taken, feedback is provided, and new relevant actions are suggested.

Next-best-action engine 200 receives the top N conditions that have been ranked by condition ranker 240 (along with a probability for each), the derived factors 54 from the patient medical record or clinician-patient encounter, as well as all possible pertinent diagnostic factors and tests for each top condition. All of these pertinent diagnostic factors and tests may have known values (due to the derived factors 54) or may be simply unknown at this point in time. By way of example, if a possible diagnostic factor for a particular condition is "iron deficiency," but it is unknown at this point in time if the patient has an iron deficiency because that laboratory test has not been performed yet, then the diagnostic factor of "iron deficiency" received by next-best-action engine 200 will have a value of "unknown" rather than a value of "present" or "not present." All of the possible diagnostic factors for a particular condition come from AIM-KB 43, and routed to the next-best-action engine by being carried into the Condition Ranker 240 from the Probability Matrix 230. Next best-action engine 200 also uses each of the top N conditions in order to query treatment probability matrix 260 via treatment ranker 270 to determine a ranking of possible treatments that may also be output as next best actions 56.

As will be explained in greater detail below, the next-best-action engine 200 processes all these inputs using models 210 in order to output results 56 which include the top N conditions (each with a probability), the known (present or not present) diagnostic factors for each condition, the tests (examinations or investigations) performed, and a ranked list of the next best actions for each condition (essentially, a list of the unknown clinical factors for a particular condition as well as treatments that have not yet been performed, and a list of tests yet to be performed).

Next-Best-Action engine 200 is a computer science-based set of models, which takes as input the outputs from Information Extraction Engine 110 and Prediction Engine 112 including but not limited to Factors 54, Condition Ranker 240, Treatment Ranker 270, and Models 210, and provides a set of clinically-relevant next best actions and strength of match (probability) of the factors 54 matching a condition. In one embodiment, NBA Engine 200 outputs the top N conditions and the top N actions not yet determined (unknown) as present or not for the top N conditions, with each such action shown in order of importance weighting from the probability matrix. One type of action is history taking or physical examination (clinical factors). Another type of action is a diagnostic test. Another type of action is a treatment. The NBA engine can also make use of multiple machine learning techniques including those described in models 210 to suggest next best actions.

Models 210 uses AIM-KB 43 combined with multiple machine learning and data science techniques for next-best-action optimizations. These models include but are not limited to reinforcement learning models such as multivariate multi-armed bandit models for highlighting anti-bias suggestions e.g., where a clinician may be at risk of intrinsic human bias resulting from the complexities of healthcare delivery and the practice of medicine due to a context such as a patient with a new condition to them, fatigue in the day, or prior clinical presentations; and/or experiencing known healthcare systematic challenges such as cognitive workload and limited time per patient, as well as deep reinforcement learning including MCTS (Monte Carlo tree search) models to further optimize next-best-actions for diagnosis and treatment across pathways, with policies configurable by the user.

Off-Line Factor Review Process

Figure 2:
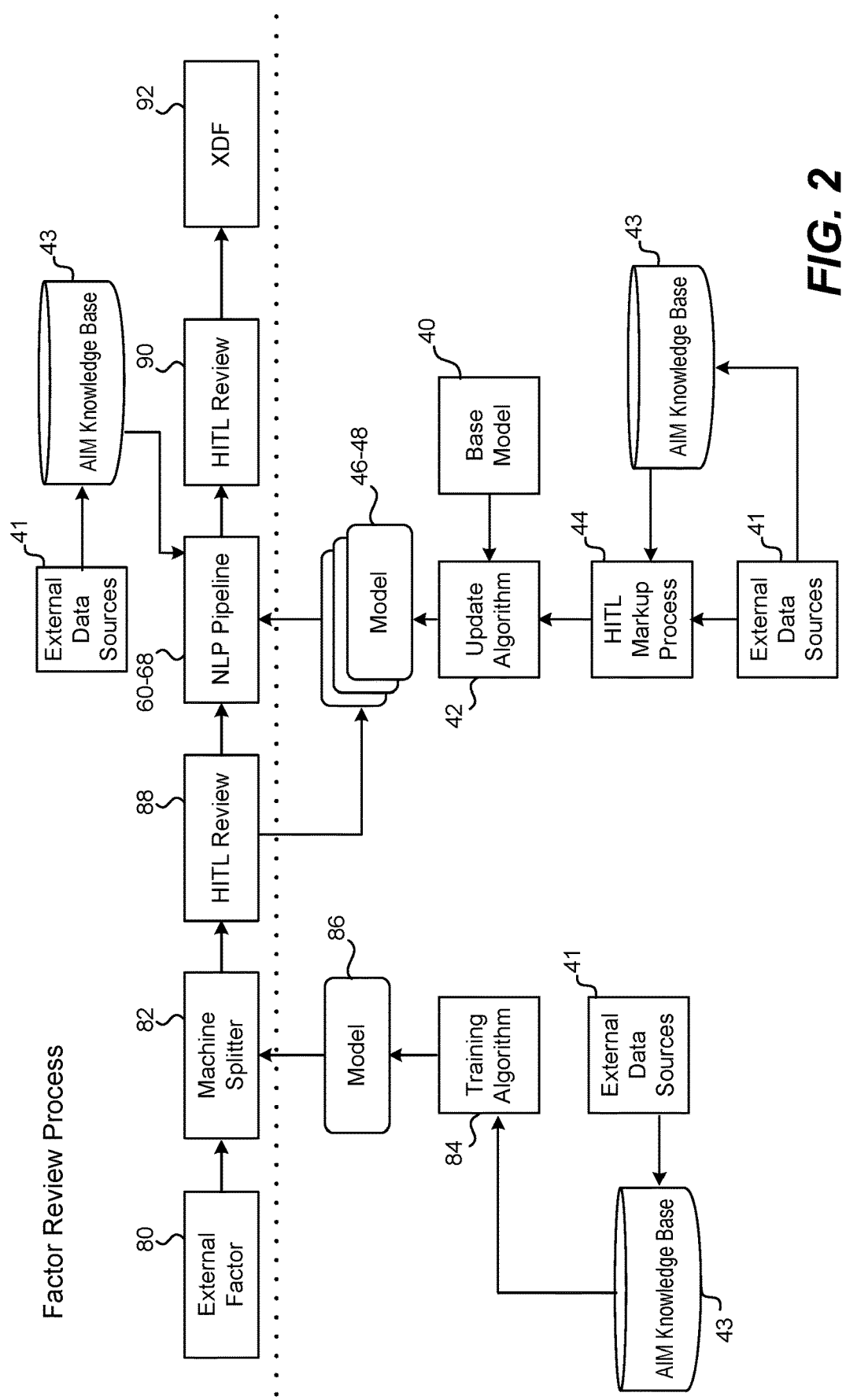
FIG. 2 illustrates an off-line factor review process that refines diagnostic factors from external data sources to better enable their recognition during real-time operation and that improves models used by the NLP pipeline to better understand words, semantics and context in input text.

FIG. 2 illustrates an off-line factor review process that refines diagnostic factors from external data sources to better enable their recognition during real-time operation and that improves models 46-48 used by the NLP pipeline to better understand words, semantics and context in input text 52. Essentially, the NLP pipeline 60-68 and its related models are used off-line to produce diagnostic factors that will be more recognizable by the NLP pipeline during real-time operation. The process includes a review of tests as well; e.g., the review includes a review of synonyms, reference values (which may be different by age, gender, time of day), etc.

Shown are components 41-48 from FIG. 1 as well as NLP pipeline 60-68. External factors 80 are raw format diagnostic factors taken from external data sources 41 before they are massaged into a format more recognizable by the NLP pipeline and its models. Machine splitter 82 is an algorithm that may split complex diagnostic factors into two or more discrete diagnostic factors to make them more recognizable. By way of example, a raw diagnostic factor "X or Y" may be split into two discrete diagnostic factors "X" and "Y" as opposed to a raw diagnostic factor "X and Y" which may remain in that format as it requires both "X" and "Y" be present. Such processing makes natural language processing more accurate. For example, the factor "black or Hispanic ancestry" is split into two factors, "black ancestry" and "Hispanic ancestry."

HITL (human in the loop) review 88 makes corrections to these diagnostic factors such as adding information that a human would infer from the condition, e.g., in the case of the condition Bells palsy modifying the factor "involvement of all nerve branches" to "involvement of all unilateral facial nerve branches."

These corrected diagnostic factors are then fed either into NLP pipeline 60-68 or into its models 46-48 to produce recognized diagnostic factors which are then fed into another round of HITL review 90 which performs corrections such as those mentioned previously. Finally, these resulting cross-condition diagnostic factors (XDF) 92 are output and may be used by the factor ranker 220 and by the NLP pipeline to better recognize not only diagnostic factors from external data sources 41 but also verbatim diagnostic factors from text 52. The XDFs may be stored back with the External Data 41 before use by factor ranker 220.

Diagnostic Glass Application

Figure 3:
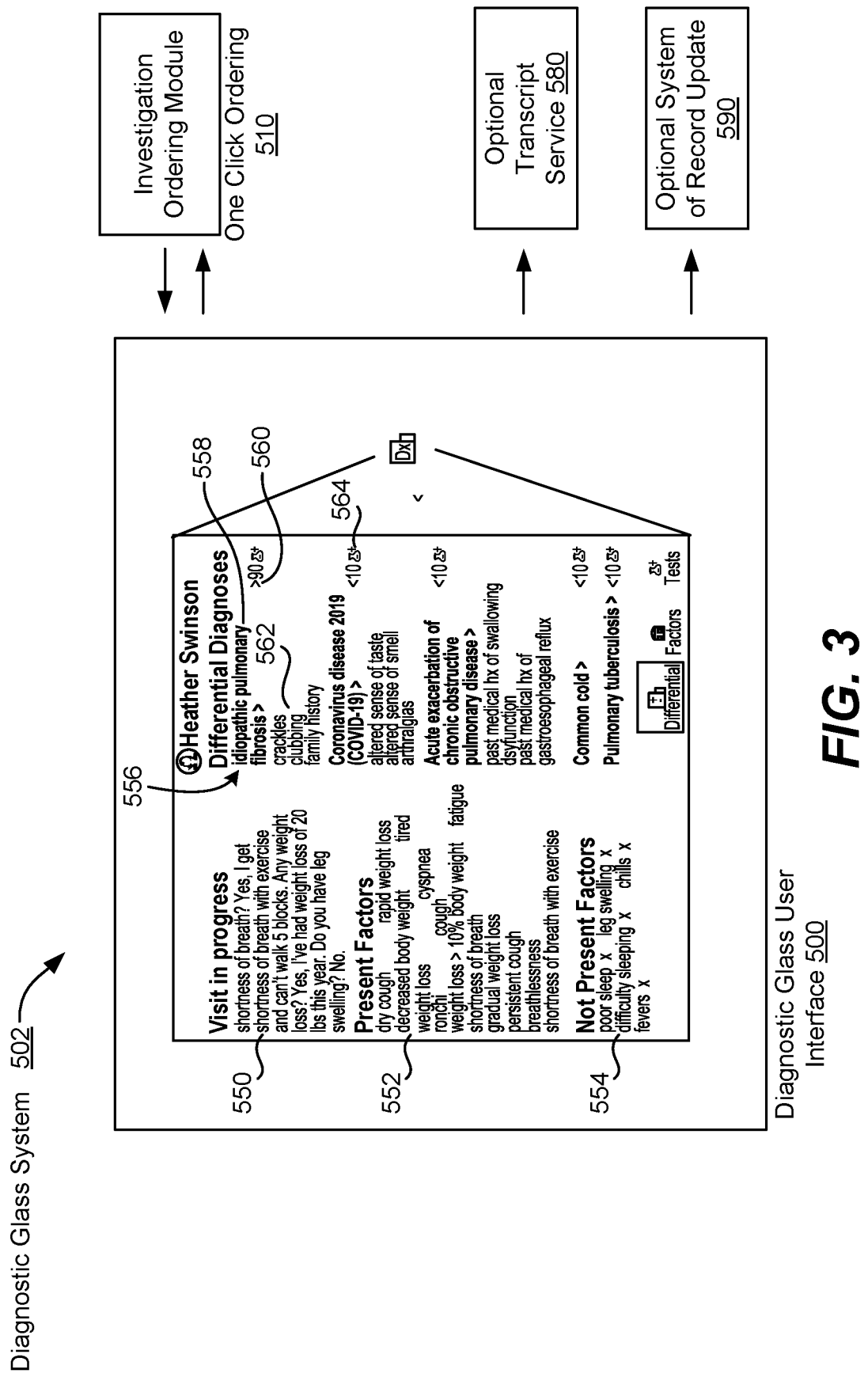
FIG. 3 illustrates one embodiment of a diagnostic glass system including the diagnostic glass user interface.

FIG. 3 illustrates one embodiment of a diagnostic glass system 502 including diagnostic glass 500 user interface. Shown is a transcription 550 (via speech recognition) of a conversation between the patient and physician (which may be in person, over the telephone, over a computing device, via telemedicine, etc.), a list of present diagnostic factors 552 of the patient, and a list of not present factors 554. Also shown is a list of differential diagnoses 556 (probable conditions) of the patient, each condition including condition name 558, a probability that the condition is present 560, and a ranked list of unknown diagnostic factors 562 that if present would indicate more strongly that the patient has that condition or conversely if know to be absent a lower probability. These unknown diagnostic factors 562 are thus the output next best actions that the clinician should attempt to determine are present or not, by way of questions, examination, etc., and are listed in order of importance. By way of example, the next best action for COVID-19 is to determine whether the patient has an "altered sense of taste." Each beaker symbol 564 for each condition is an icon that, when clicked upon, lists the next best action laboratory tests, examinations or investigations that should be performed upon the patient to help confirm or refute the presence of that particular condition. See FIG. 10E for an example. Of course, other symbols, words or functionality may be used to list next best tests.

One-click-ordering module 510 implements a method whereby a clinician can click once on one or more tests or investigations (e.g., shown at 842) they wish to run as shown by 500 (and which have been generated by 200 and relevant data sources), and which automatically populates data into the customer clinical workflow to order that test or investigation (including the relevant ICD coding) without the clinician having to enter any further data. Various steps are used by the one-click-ordering module 510 including but not limited to prior authorization for a given investigation, as well as submission of the orders to the test providers.

Optional Transcript Service 580 is an optional service that provides a digitized transcript of the clinician encounter, for patient, physician, or other relevant purposes, both full and key points summarized.

Optional System of Record Update 590 is an optional service that automatically updates the EHR System of Record 140 from the diagnostic glass 500 (in addition to 510); it leverages 110 by creating a note or other EHR entry containing the extracted factors and their statuses.

Flow Diagram—Determine Next Best Action

Figure 7A:
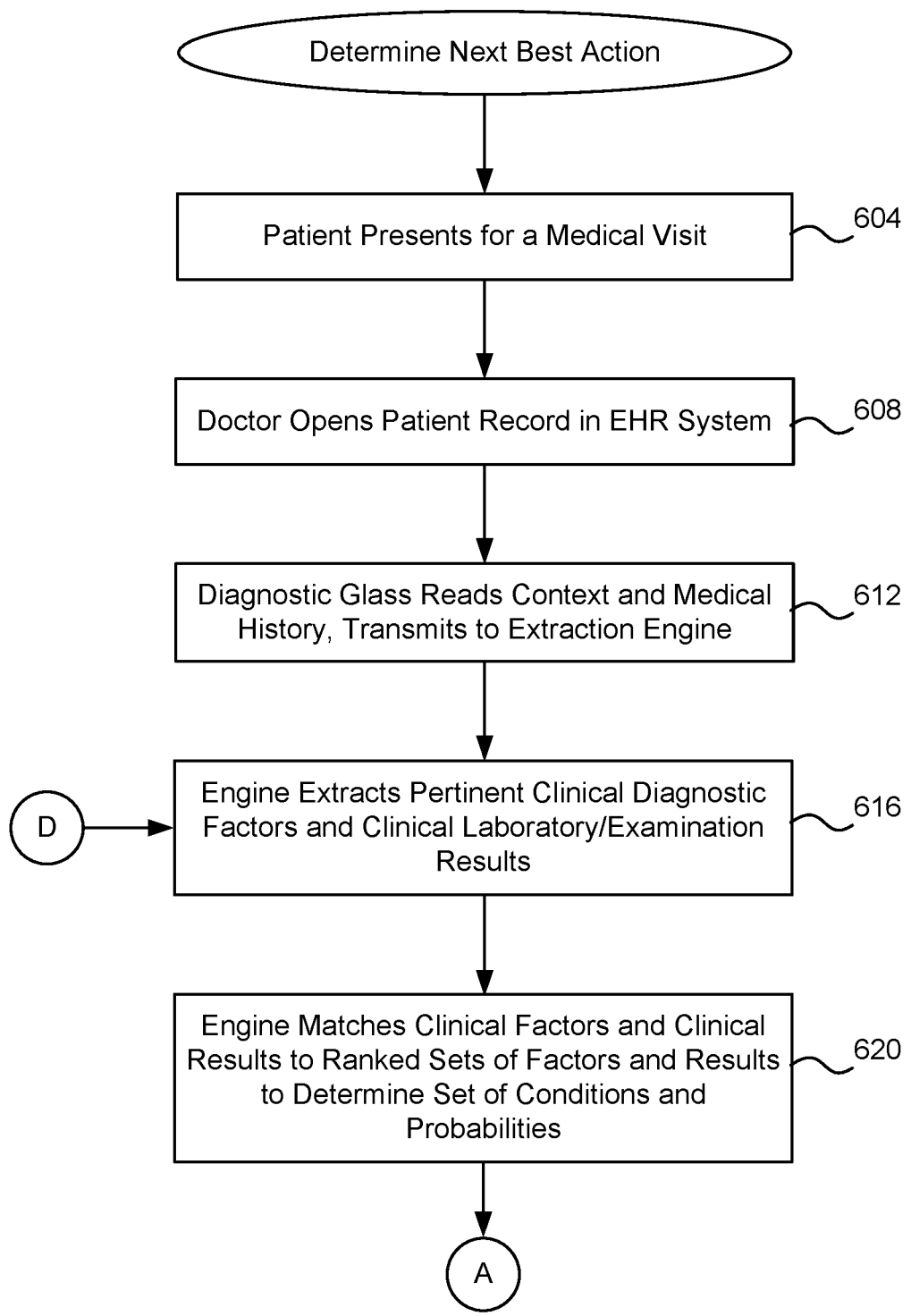
FIG. 7A is flowchart description of one embodiment of the initiation phase of the next-best-action system
Figure 7B:
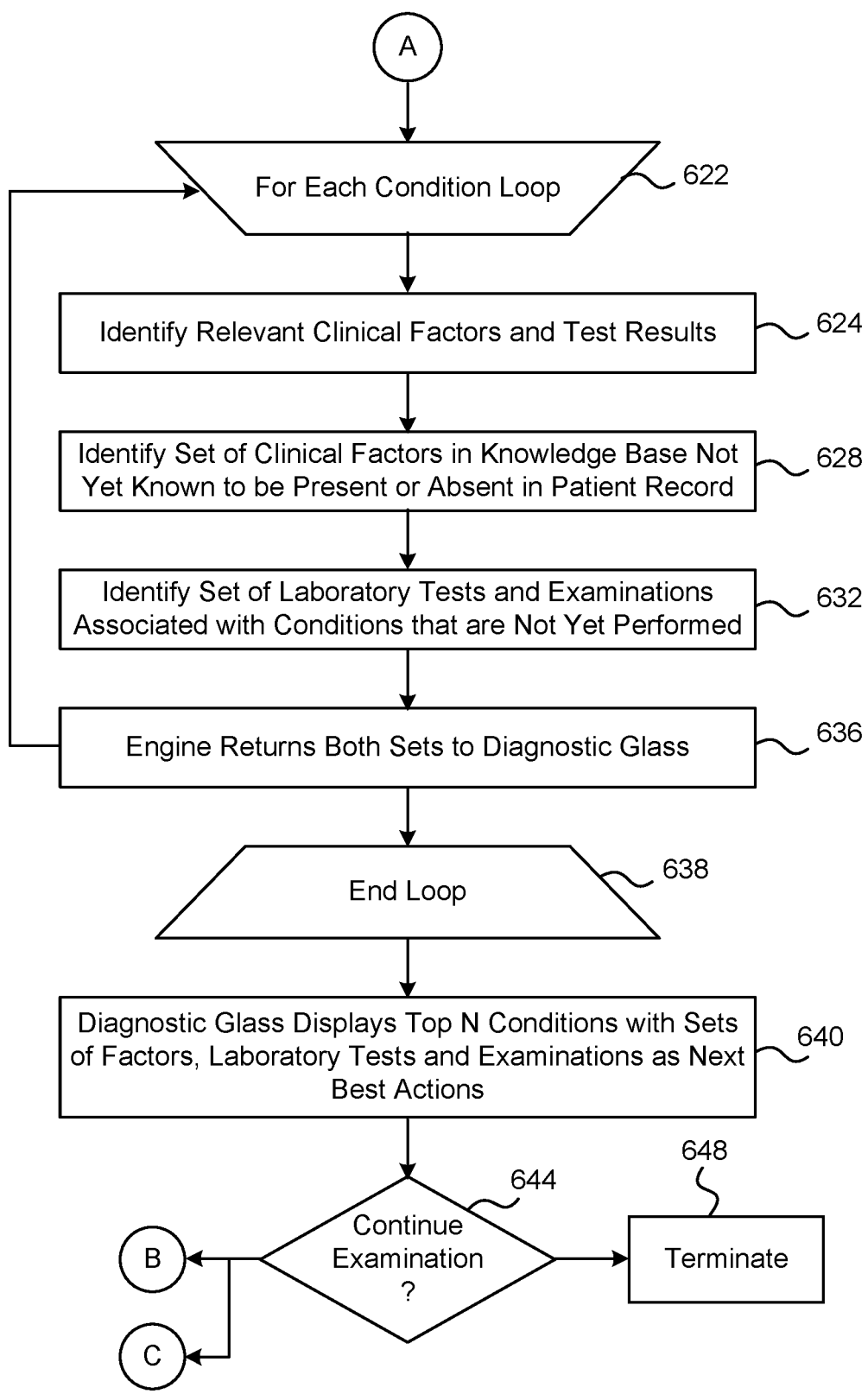
FIG. 7B is a flowchart description of one embodiment of the real-time operating phase of the next-best-action system

FIGS. 7A and 7B are a flow diagram describing one embodiment by which a next best action is determined for a particular patient. In a first step 604 a patient presents for a medical visit with a clinician and this may be an in person visit, the client may be remote and may participate by telephone or computer, or any other suitable telemedicine scenario may be used. In a next step 608 the clinician uses the EHR system user interface 160 to open the patient's electronic chart in the EHR system. Next, in step 612 the diagnostic glass application (which may be integrated with the EHR system) reads the current patient context from the EHR system, i.e., the patient's medical history, including all text but preferably excluding images and waveform signals, and transmits this text to the information extraction engine 110.

How much information in the patient's medical history that is read from the EHR system is configurable within the next-best-action system 10. While it may be appealing to read in the entire medical history, it is likely that diagnostic factors experienced ten years ago are not relevant to an acute condition the patient presents with today. Accordingly, input of the patient's medical history may be filtered by time, that is only the past X months of history may be input. The time range to be input (e.g., the past week, past month, past year) may be hardcoded into the next-best-action system, may be represented by one of more parameters that are configured by the customer entity (i.e., by the hospital, not by the clinician), or may be settings that may be adjusted by the clinician using the diagnostic glass. By way of example, should a patient present with an acute condition that he or she is positive began "just about a week ago," the clinician may decide to limit history intake for the past month or so, rather than reading in the entire patient history. On the other hand for a patient with a chronic disease of ten years or more, the clinician may decide to read in the entire medical history. Such hard coding, parameters or adjustable settings can specify a date range and then filter the medical record using the dates of clinical visits, clinician notes, tests, etc.

In step 616, using information extraction engine 110, engine 200 receives all pertinent positive and negative clinical diagnostic factors and all pertinent laboratory test, examination and investigation results present in the patient's EHR record for the previous relevant time period, as possibly limited by any hardcoded date values, parameters or settings as discussed above.

In general, the record may reflect that a patient does have a particular diagnostic factor (present), may reflect that the patient does not have a particular factor (not present), or may be silent on a particular factor, meaning that the status of that factor is unknown. Laboratory test results will indicate ranges, the presence or not of certain substances, etc., as is known in the art. Investigation results will indicate results from a particular investigation.

Next, in step 620, engine 200 using condition ranker 240 matches these pertinent clinical factors and test results from step 616 to the ranked sets of factors and results found in the factor probability matrix 230 in order to determine a set of likely conditions and their probabilities. By way of example, if a patient exhibits 7 out of 10 diagnostic factors that are most probable for a particular condition A, but only exhibits 3 out of 10 diagnostic factors for a particular condition B, then the output of step 620 will list condition A with a higher probability than condition B.

For each determined condition then with a greater than de minimis probability, a loop 622 begins and executes the following steps. Typically, any condition with a probability greater than 10% will be processed. Typically, any probability less than 10% is shown as "<10%." This minimum amount is configurable.

In step 624 engine 200 identifies the clinical factors and test results relevant to the current condition that are known to be present or that are known to be absent in the patient record. In step 628 engine 200, using Operational Data 49 and results from step 624, identifies the set of clinical factors for the current condition that are not yet known to be present or absent in the patient record. In step 632 engine 200, using external data sources 41 and results from step 624, identifies the set of laboratory tests, examinations and investigations for the current condition that have not yet been performed according to the patient record. Next, in step 636 engine 200 returns both sets from steps 628 and 632 to the diagnostic glass 500. These two sets of clinical factors and laboratory tests, investigations, examinations are thus relevant for a particular condition but they are either unknown or have not yet been performed and are therefore referred to as the next best actions. Engine 200 will know which are the relevant factors for a particular condition because they will be the ones with non-zero entries in the probability matrix.

Finally, in step 640 the diagnostic glass displays the top N conditions (configurable) each with an associated probability and the sets of unknown factors and unperformed laboratory tests/examinations/investigations as the next best actions. By way of example, as shown in FIG. 3, condition 558 (Idiopathic pulmonary fibrosis) lists three clinical factors, "crackles, clubbing, family history" whose status is unknown and which are the next best actions. In addition, the beaker symbol when clicked upon will show any unperformed laboratory tests, examinations or investigations that should be the next best actions as well. Preferably, the listing of the next best actions (whether clinical factors or laboratory tests, examinations or investigations) are listed in the order of their importance to a particular condition, such as by using their ranking in the factor probability matrix or the ranking in Operation Data 49 (using AIM-KB data).

Other techniques for displaying this information may also be used. For example, the number of conditions presented may be configured in a variety of ways including but not limited to a specific number of conditions or by using a specified probability threshold. Or, the conditions may be ordered by their probabilities established by engine 200. The information may be displayed within diagnostic glass 500, within a similar standalone product, or integrated with the EHR system. The pertinent present, not present and unknown clinical factors associated with a particular condition may be displayed with an indication as to their particular state. The unperformed laboratory tests, examinations and investigations may also be listed with their current state (i.e., unperformed). The next best actions either as clinical factors or laboratory tests/investigations/examinations may be presented either per condition or in the aggregate. The presentation of the information by the diagnostic glass user interface may be textual, graphical, audio, video, a combination of the above or in another appropriate format.

In step 644 the clinician decides whether to continue with the examination (discussed below) or to terminate the current session. If he or she decides to terminate, then the clinician signs out of the patient chart in the EHR system which results in the patient context being cleared. In response, the diagnostic glass 500 then clears the patient state and patient information from its display leaving basically an empty state or blank screen.

In addition to obtaining factors and test results from the patient's electronic health record, next-best-action system 10 may also obtain this information in real time as the clinician examines the patient. Indeed, in an alternative embodiment, the below steps may be performed before steps 608-612 in which case system 10 may base its conclusions solely upon information gleaned by the clinician in the course of the patient examination. Or, the below steps may be performed and then steps 608-612 obtain information from the patient's electronic health record. In a preferred embodiment, as described immediately below, steps 608-612 obtain information from the patient's electronic health record, preliminary conclusions are drawn, and then the clinician continues with the patient examination in order to identify new factors, results, etc., in real time as he or she interacts with the patient.

Flow Diagram—Continue Examination by Typing Information

Figure 7C:
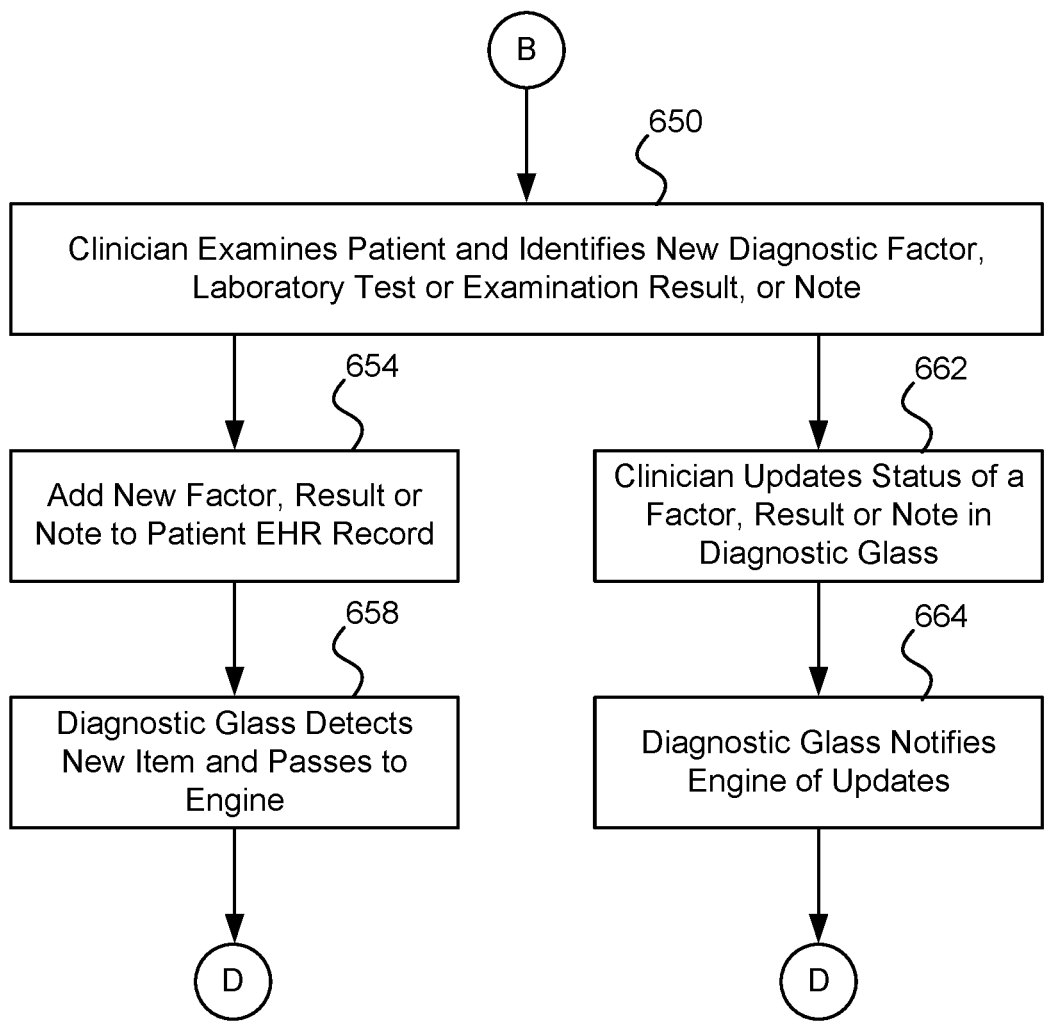
FIG. 7C is a flow diagram describing one embodiment by which the clinician interviews and examines the patient and enters new information directly into the EHR system or into the diagnostic glass by typing, using a touchscreen, computer mouse, etc.

FIG. 7C is a flow diagram describing one embodiment by which the clinician interviews and examines the patient and enters new information directly into the EHR system or into the diagnostic glass 500 by typing, using a touchscreen, computer mouse, etc.

Figure 7D:
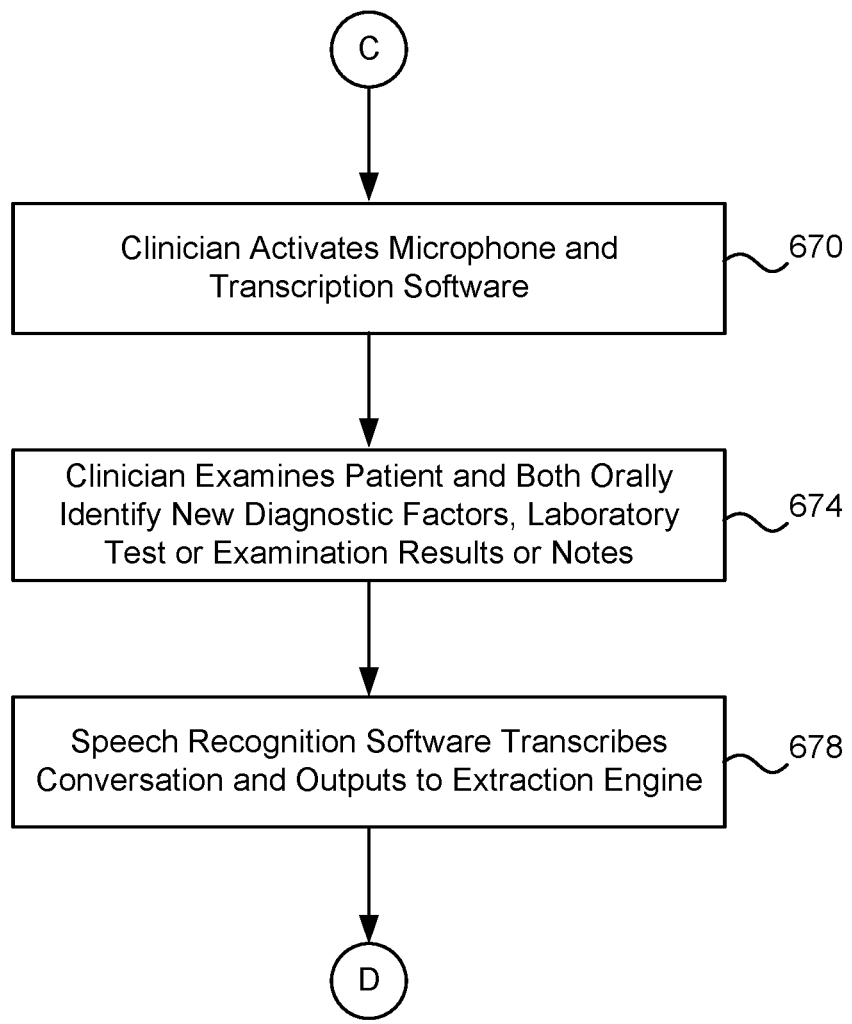
FIG. 7D is a flow diagram describing one embodiment by which the clinician interviews and examines the patient and their conversation is transcribed and new information is entered automatically into the system.

FIG. 7D is a flow diagram describing one embodiment by which the clinician interviews and examines the patient and their conversation is transcribed and new information is entered automatically into system 10.

Preferably, the clinician either decides to proceed with the examination with the microphone off and enters all new information by typing (FIG. 7C), or decides to turn the microphone on and let the transcription software transcribe the conversation and enter all new information automatically (FIG. 7D). In this manner, the rest of the examination proceeds either with the microphone off or on. Alternatively, the clinician may decide to turn the microphone on from time to time and let the transcription software recognize their speech, transcribe it automatically and enter information that way. By way of example, the clinician may start with the microphone off while he or she enters laboratory test results or written notes by typing, but may then turn the microphone on when he begins to ask the patient specific questions such as "do you have a fever?", "do you have an altered sense of smell?", etc. In this manner, the clinician is in charge of when to use the external microphone for maximum efficiency.

Discussion begins with the flow of FIG. 7C. Accordingly, in a step 650 the clinician proceeds with the clinical examination of the patient and identifies new clinical factors, new laboratory results, new investigation results, or clinical notes that he or she feels should be entered into the medical record.

By way of example, the clinician may determine patient symptoms by querying the patient if he or she has shortness of breath, has any weight loss, has any fevers or chills, etc., in order to identify the presence or absence of any particular clinical factors. In particular, using the next best actions output by the system in step 640, the clinician may query the patient using the top factors that as of yet are unknown, for example, asking the patient if he or she has "crackles," an altered sense of taste, or a past medical history of COPD (chronic obstructive pulmonary disease) (using the top next best actions shown in FIG. 3).

In addition, the clinician may determine patient signs by performing a physical examination of the patient in order to determine diagnostic factors such as blood pressure, temperature, blood oxygen, reflexes, skin color, etc. Further, the clinician may perform, order, or have performed laboratory tests that provide laboratory results such as ranges for components of the patient's blood, etc. Some laboratory tests may be performed almost immediately or in the course of a number of minutes while the patient is being examined, while other tests may take some time before results are returned. In any case, these laboratory test results may be input into the system as described below when the results are available. The clinician may also order investigations which also likely will take time and their results will be input into the system when available.

The clinician may also create a new clinical note for input into the EHR system and these clinical notes are typically entered by typing or selecting structure input fields in the EHR's user interface.

Next, in step 654 the clinician adds these newly determined clinical factors, investigation results, laboratory test results or new clinical notes to the patient's EHR record using EHR user interface 160. In step 658 the diagnostic glass 500 detects that new information is present using EHR agent 145 and proceeds to pass this new information to prediction engine 112 via information extraction engine 110.

Next, control moves to step 616 as previously described in which information extraction engine 110 proceeds to extract the pertinent clinical factors and laboratory and investigation results (all considered diagnostic factors) from the new information. The flow continues as before in which step 620 matches factors and results; new conditions or conditions with new probabilities may be surfaced, steps 624-636 are performed using the new conditions, and again in step 640 the diagnostic glass displays top conditions and next best actions, all based upon the recent information entered by the clinician during the physical examination of the patient.

Alternatively, instead of entering the new information into the patient's EHR record in step 654, the clinician in step 662 enters the new information into the diagnostic glass 500 by updating the status of a particular clinical factor, adds a new laboratory test or investigation result, or adds a new note. By way of example, referring to FIG. 3, the clinician may change the status of any of the factors 562 by simply clicking upon one of them and changing the status to either "present" or "not present." Any of the factors shown at 552 or 554 may also have the status changed by selecting the factor and choosing an option. As will be appreciated by those of skill in the art, a factor may be chosen to be present, not present or unknown via various user interaction techniques such as radio buttons, check boxes, use of highlighting, drop-down menus, etc. A factor previously indicated as present or not present may also be changed to unknown.

In a similar fashion, investigation results may be added or changed by entry into an EHR note. And, laboratory results may be added or changed by clicking upon the beaker icon associated with a particular condition and using known user interface techniques to add a value or range for a particular laboratory test or changing the results of a laboratory tests.

In step 664 the diagnostic glass 500 proceeds to pass this new information to engine 112 via information extraction engine 110. Next, control moves to step 616 as previously described in which information extraction engine 110 proceeds to extract the pertinent clinical factors and laboratory and investigation results from the new information. The flow continues as before in which step 620 matches factors and results; new conditions or conditions with new probabilities may be surfaced, steps 624-636 are performed using the new conditions, and again in step 640 the diagnostic glass displays top conditions and next best actions, all based upon the recent information entered by the clinician during the physical examination of the patient.

Flow Diagram—Use of Transcription Software

Discussion now continues with the flow of FIG. 7D. As mentioned earlier, the clinician may decide that it is most efficient to use an external microphone in order to capture the conversation and to have that conversation transcribed. Although the patient and clinician may be in the same room, this embodiment also works well where the patient is remote (i.e., via telemedicine) and the patient's voice can be picked up by the microphone.

Accordingly, in a step 670 the clinician activates external microphone 130 and transcription software 120. The microphone and transcription software may also be activated automatically by the diagnostic glass 500 when the encounter begins, according to settings configured in the diagnostic glass.

As known to those of skill in the art, many suitable microphones exist for capturing human speech for transcription including lavaliere microphones, head-mounted microphones, desk-mounted microphones, microphones integrated into a desktop or laptop computer, or microphones of a mobile telephone. If the microphone is of high quality and positioned correctly a single microphone may be used, although a microphone for each of the clinician and patient may also be used. Transcription software 120 is executing upon a mobile device or computer of the clinician and may be any of a wide variety of speech recognition software that is able to capture human speech, transcribe it, and output the transcribed speech into common electronic text formats.

In a next step 674 the clinician begins to examine the patient and orally ask questions and orally explain laboratory test results or investigation results, or explain a new note. Accordingly, the conversation between the clinician and patient reveals new diagnostic factors, new laboratory results, new investigation results, or other notes. By way of example, the clinician may elicit diagnostic factors by asking questions such as "do you have a headache?", do you feel nauseated?", etc., and may cause results to be transcribed by making statements such as "I see that your skin has a light yellow color," "your reflexes appear normal," "your pupils are slightly dilated," etc. The clinician may even cause new laboratory test results to be transcribed by reading results such as "your white blood count is x," "your platelet level is y," "your hemoglobin value is z," etc., or may cause investigation results to be transcribed by reading a result such as "your pelvic x-ray did not show anything unusual."

The clinician may also change the status of previously identified diagnostic factors by using keyword commands simply by restating the current status of a particular diagnostic factor. By way of example, if the diagnostic glass indicates the diagnostic factor that the patient does not have a headache (which factor may have come from the chart, from an earlier conversation, a misstatement by the patient or misinterpretation by the clinician), but now becomes clear that the patient does have a headache, the physician may simply state "the patient does have a mild headache," and this phrase will be transcribed, input into engine 110 which will then change the status of the diagnostic factor "mild headache" from "not present" to "present."

Continuously, in step 678 the speech recognition software recognizes and transcribes this conversation and outputs text in the form of an electronic document in any suitable format into information extraction engine 110. This transcribed conversation may be output continuously, phrase by phrase, as it occurs, or the transcription software 120 may output portions of the conversation periodically or after a suitable pause in the conversation. As shown at 550 in FIG. 3 in the diagnostic class 500, the entire transcribed conversation may appear for easy reference by the clinician, although the entire transcribed conversation need not be shown. What has been extracted from this transcribed conversation by extraction engine 110 are the presence or absence of diagnostic factors 552 and 554, as well as laboratory tests and examination results (not shown).

Next, control moves to step 616 as previously described in which information extraction engine 110 proceeds to extract the pertinent diagnostic factors and laboratory and examination results from the transcribed conversation, similar to how it extracted this information from the text of the patient record in the EHR system. The flow continues as before in which step 620 matches factors and results; new conditions or conditions with a recomputation of probabilities may be surfaced, steps 624-636 are performed using the new conditions, and again in step 640 the diagnostic glass displays top conditions and next best actions, all based upon the recent conversation between the clinician and patient during the physical examination of the patient.

Flow Diagram—Determine Next Best Treatment

FIG. 4 shows a simple example database 300 showing a condition followed by list of ranked possible treatments. Shown at 310 is a list of treatments for adults with pain, 320 shows treatments for adults without pain, and 330 shows treatments for ongoing conditions.

Figure 8:
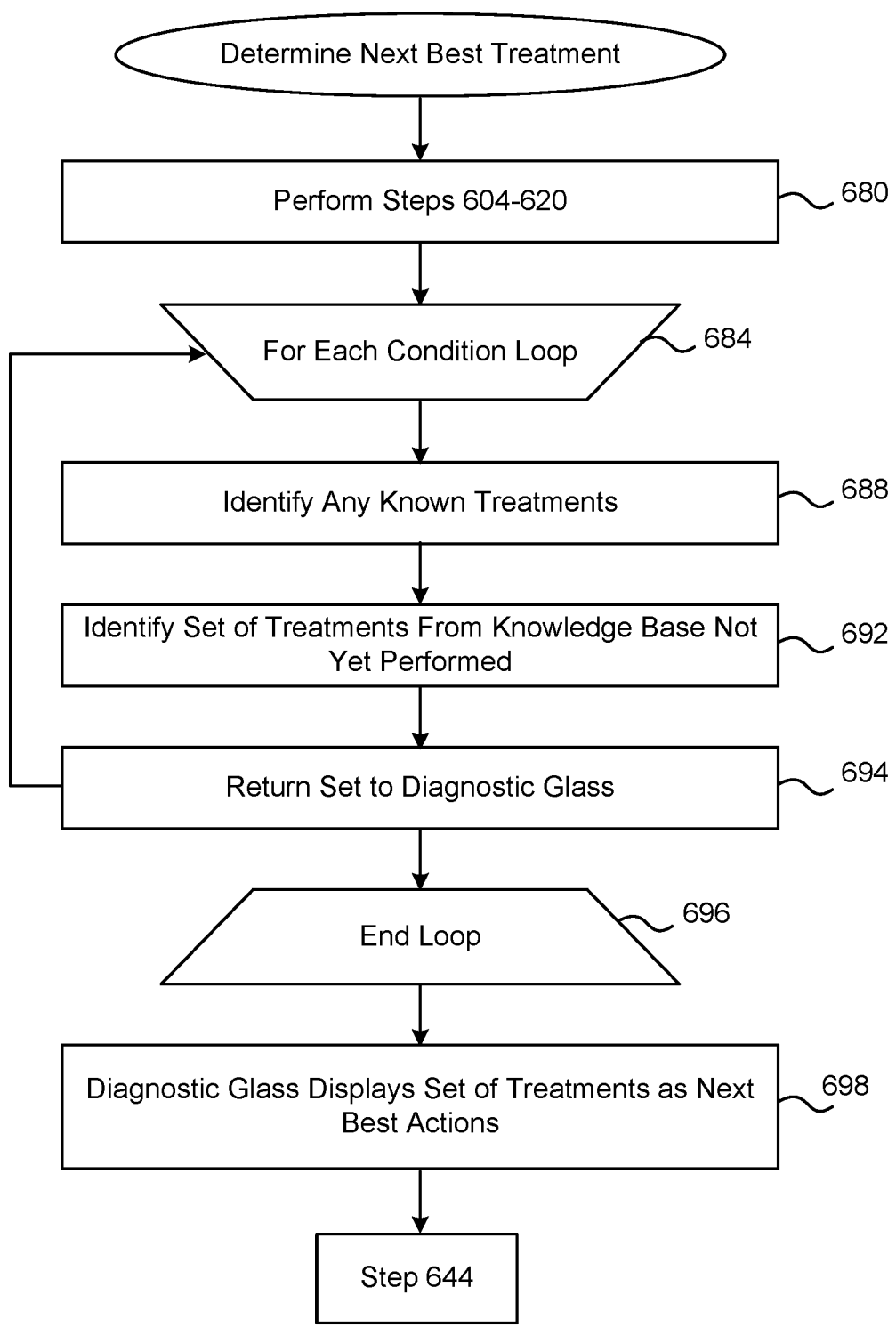
FIG. 8 is a flow diagram describing one embodiment by which a next best treatment is determined for a particular patient.

FIG. 8 is a flow diagram describing one embodiment by which a next best treatment is determined for a particular patient. As described above, system 10 outputs next best actions for particular conditions such as diagnostic factors that should be determined or laboratory tests and investigations that should be performed. Included within the meaning of "next best action" is also a particular treatment or treatments that should be applied for a particular condition. In addition to the next best actions shown in FIG. 3, for example, treatments may also be output and displayed for particular conditions, thus enabling the clinician to use his or her best judgment in deciding whether to attempt to determine more diagnostic factors, perform more tests, or simply choose a particular treatment and see if that improves the patient's condition.

Although FIG. 8 and a determination of next best treatments is shown in a separate flow diagram, one of skill in the art will appreciate that this flow may be integrated into the flows of FIGS. 7A-D and that any next best treatments may be displayed in the diagnostic glass along with any next best diagnostic factors, laboratory tests and investigations, all to enable the clinician to make the best choice in his or her judgment.

Initially, steps 604-620 are performed as described above resulting in a determination of the set of possible conditions that the patient may have. Next, in step 684, similar to the loop of step 622 (or integrated within that loop), a loop begins that considers each condition with more than a de minimis probability. Typically, any condition with a probability greater than 10% will be processed. Typically, any probability less than 10% is shown as "<10%." This minimum amount is configurable.

In step 688 engine 200 identifies any treatments relevant to the current condition that are known to have been tried already. By way of example, the patient's medical record in the EHR system may list treatments that have previously been tried for a particular condition or the patient may have told the clinician that a treatment has already been tried (which information is typed in by the clinician or captured by the transcription software as discussed above). Typically, a treatment is associated with a status such as "performed," "active," "scheduled" or "unknown." Those treatments identified as being "performed," "active" or "scheduled" are identified in step 688 as being a current, known treatments.

In step 692 engine 200, using Operational Data 49 and results from step 688, identifies the set of treatments for the current condition that have not yet been tried, e.g., by using the database of FIG. 4. By way of example, if a particular condition in a database lists eight possible treatments, and of those eight, six currently appear in the patient's record having a status of "performed," "active" or "scheduled," then the remaining two treatments have not been tried yet and these two are placed into the set of treatments not yet performed. Typically, an entry in a database of sources 41 for a particular condition will list treatments in the order of least costly to most costly as described above.

Next, in step 694 engine 200 returns this set of treatments to the diagnostic glass 500. This set of treatments is thus relevant for a particular condition but have not yet been applied and are therefore also referred to as the next best actions. The loop ends in step 696 when all conditions have been considered.

Finally, in step 698 the diagnostic glass displays the top N conditions each with an associated probability and the sets of possible treatments as the next best actions. Preferably, the listing of these next best actions are listed in the order of their least cost for a particular condition, such as by using their ranking as listed in a database of external data sources 41. At this point, control returns to step 644 and the clinician may decide to continue with the examination or terminate the session. As described above, the clinician may continue with the examination and solicit more information including querying the patient about other treatments that have been performed and the system will continue to recompute conditions and probabilities based upon any new information.

Example Knowledge Base Record

As mentioned earlier, external data sources 41 may be comprised of numerous different databases and data sources that all associate certain clinical factors, laboratory tests and investigation results with a particular condition that is indicated by these factors, tests and results. These data sources may also include drug interactions, care pathways and treatment data, for example, which treatments to consider in which order for single conditions and multiple conditions (comorbidities).

FIGS. 9A and 9B illustrate a simple example of a single record in a database of external data 41. The data in this example is from BMJ Best Practice US, and from the BMJ Best Practice Evidence-Based Medicine knowledge base. This is one external data source that the invention uses. This example describes a particular condition and its associated clinical factors, laboratory tests and investigations. Of course, there will be many thousands of conditions in a particular database and there may be many databases and data sources.

Shown at 702 in FIG. 9A is a particular condition and below are the key diagnostic factors 704, followed by other diagnostic factors 706 and finally by weak diagnostic factors 708. Thus, this record lists the high probability diagnostic factors 704, that, if present, tend indicate that it is more likely that the patient has the particular condition 702. In fact, in this example (and in other databases as well) the diagnostic factors 704 are themselves listed in order from highest probability to lowest. The other diagnostic factors 706 have a lower probability in that if present, they are less likely to indicate that the patient has a condition, and finally, the weak diagnostic factors 708 are even less likely to indicate that the patient has a condition if a factor is present.

Shown at 702 in FIG. 9B is the same condition and below are the first investigations to order 712, followed by other investigations to consider 714. Thus, this record lists the high probability investigations 712, that, if ordered, or more likely to indicate whether or not the patient has the condition, while the other investigations 714 are less likely to indicate whether or not the patient has the condition. Similar to the above, these investigations 712 and 714 are listed in order from highest probability to lowest. Generally, in the probability matrix the presence or absence of a diagnostic factor will indicate the probability that the condition is present, the more of such factors the more likely it is that the patient has the condition.

Example Interaction Between Clinician and Next-Best-Action System

FIGS. 10A-10I illustrate an example interaction between a clinician and next-best-action system 10 during a clinician-patient encounter. Shown are screenshots of a specific EHR user interface 160 as well as of the diagnostic glass user interface 500.

FIG. 10A illustrates the beginning of the example interaction in which a clinician has opened an EHR system which displays its user interface 800 having a patient finder tab 802 showing any number of patients 804 whose medical records may be opened. Shown on the right-hand side is an icon 501 for the diagnostic glass 500 application which is currently in a minimized state. In this example, The diagnostic glass in this example is a separate application that is running in the same window as the EHR user interface. It occupies a portion of the same screen as the EHR interface. In an alternative embodiment, not shown, the diagnostic glass application is integrated with the EHR system in that the EHR user interface shows the diagnostic glass icon, allowing it to be opened from within the EHR system. In either embodiment, the diagnostic glass application can read information from the EHR system and can input information to the EHR system as will be discussed below.

FIG. 10B illustrates the example interaction after the clinician has opened the diagnostic glass application 500. The clinician may simply click upon icon 501 which opens window 811 with which the clinician will interact with the next-best-action system 10 via the diagnostic glass user interface. Window 811 is blank as no patient has been selected yet. It is important to note that is it not necessary for the clinician to open or expand the Diagnostic Glass prior to its use.

FIG. 10C illustrates the example interaction after a patient has been selected and her context has been loaded. Once a patient has been selected (e.g., by clicking on the patient name in screen 804) her medical record is loaded into the EHR system (from a local or remote database) is then displayed or otherwise available for use in tab 810. At the same time (or immediately thereafter) the patient's medical record is loaded into the next-best-action system via diagnostic glass 500 and the text of her clinical history is processed as has been discussed above. This processing results in window 811 being populated with the following information. Shown at 820 are any number of differential diagnoses (typically the top five), each including a probability 822 of being the condition with which the patient is afflicted. Displayed below the most likely condition 824 is a set 826 of three next best actions (clinical factors, ordered from most likely to indicate the presence of the condition to least likely) whose state is currently unknown. In other words, it is unknown at this point in time whether the patient has an altered sense of taste or smell or is fatigued. Also shown associated with condition 824 is a beaker icon 828 that, when clicked, will show the laboratory tests (or examinations or investigations) which have not yet been performed, also ordered from most likely to least likely, and which are also considered next best actions.

Although the clinician is always in charge, he or she is encouraged to consider these next best actions and to select one or more to inquire about or to perform. Typically, next best actions 826 are traditional clinical diagnostic factors that the clinician can determine by querying the patient or performing a simple and rapid examination in the office. Next best actions 828 are typically laboratory tests or sophisticated investigations that take more time to perform such as sending a blood sample to the laboratory or asking the patient to schedule an MRI. Note that these results are displayed after the next-best-action system 10 has input the patient's medical record and before the clinician has asked questions, performed an examination or input any information about the encounter.

FIG. 10D illustrates the example interaction after the clinician has selected a particular diagnosis. In this example, the clinician has clicked upon condition 824 which results in pertinent factors 838 being displayed in ranked order of relevance as well as unknown factors 839 also being displayed. Note that a pertinent factor followed by a "+" sign indicates that the factors is present while a "−" sign indicates that the factor is not present. Note also that of the factors 839 which are currently unknown, they are also ordered by their ability to indicate the presence of the condition. Typically, the next best actions are ordered by their importance in indicating that the condition could be present, in other words, if the result of a simple test could indicate strongly that the condition is present it may be ordered first.

FIG. 10E illustrates the example interaction after the clinician has selected beaker icon 828 in order to view the laboratory tests, examinations and investigations which are also next best actions. Referring back to FIG. 10C, the clinician has clicked upon beaker icon 828 associated with condition 824 which results in the display of FIG. 10E (rather than the previous display of FIG. 10D). Shown are any number of laboratory tests (or examinations or investigations) in a ranked set 842, again, ordered from most likely to indicate the presence of the condition to least likely. For instance, a result from the RT-PCR test is generally considered definitive as to whether the patient has COVID-19 and is thus listed first. By clicking upon the beaker icon next to a particular test the test may be ordered with a simple click. By way of example, should the clinician decide to order the ABG (arterial blood gas) test (requiring the collection and analysis of a blood sample), he or she simply clicks upon beaker icon 844 which results in an order for this test to be fed back into the EHR system and lodged as a pending order in the patient's medical record. Thus, with a single click a clinician may order one or more relevant tests for a patient.

FIG. 10F illustrates the example interaction after the clinician has clicked upon the factors icon. Shown at the bottom of window 811 is a differential icon 832, a factors icon 834 and a tests icon 836. Up until this point, by default, the differential icon has been selected (and highlighted) resulting in the differential diagnoses being displayed within window 811. By clicking upon factors icon 834 (which is now highlighted) all of the known diagnostic factors (present or known not to be present) in the patient's medical record are displayed. Although not shown, if the clinician were to click upon Tests icon 836 then all of the laboratory tests, examinations or investigations that have selected to be ordered for the patient are displayed.

Shown at 852 are the pertinent present factors, meaning that the patient does have these diagnostic factors. At any time the clinician may click upon a present factor 852, such as by clicking the "X" next to fever 853, because that factor is actually unknown, and thus removing that factor. Accordingly, this change in status from "present" to "unknown" will trigger a recomputation by prediction engine 112 possibly resulting in a new differential diagnosis. Essentially, factors 54 are again fed into the condition ranker 240 except that "fever" will now have a status of "unknown" instead of "present."

FIG. 10G illustrates the example interaction after the clinician has clicked upon the factors icon and has scrolled father down window 811. Shown are more present factors 852 as well as numerous not present factors 854. A not present factor 854 indicates that the patient does not exhibit this factor. Similar to the above, at any time the clinician may click upon a not present factor 854, such as by clicking the "X" next to chills 855, because that factor is actually unknown, and thus removing that factor. Accordingly, this change in status from "not present" to "unknown" will trigger a recomputation by prediction engine 112 possibly resulting in a new differential diagnosis with new conditions and probabilities. Essentially, factors 54 are again fed into the condition ranker 240 except that "chills" will now have a status of "unknown" instead of "not present."

Figure 10H:
FIG. 10H illustrates the example interaction after the clinician has activated the transcription software and external microphone.

FIG. 10H illustrates the example interaction after the clinician has activated the transcription software 120 and external microphone 130. By clicking upon a suitable user interface button the clinician turns on the microphone.

The microphone and transcription software are activated and begin recording, transcribing and feeding into information extraction engine 110 the verbatim text of the conversation between the clinician and the patient. The diagnostic glass 500 then opens window 861 which displays at 862 the transcribed conversation as well as any pertinent present factors 864 that have been derived from that transcription. The addition of any new present factor from that transcription will also result in a recomputation by prediction engine 112 possibly resulting in a new differential diagnosis with new conditions and probabilities. In fact, as shown under differential diagnoses 820, the top condition is no longer COVID-19 but now is idiopathic pulmonary fibrosis. Thus, a new, pertinent factor introduced solely by transcribing a conversation has resulted in a re-computation and a display of a new differential diagnosis. As above, if the patient indicates that he or she is no longer "tired" that factor may be removed at 865 also resulting in another recomputation.

FIG. 10I illustrates the example interaction after the clinician has activated the transcription software and microphone and has scrolled farther down window 861. In addition to present factors 864 now shown are not present factors 866. The addition of any new not present factor from that transcription will also result in a recomputation by prediction engine 112 possibly resulting in a new differential diagnosis with new conditions and probabilities. As above, if the patient indicates that he or she is unsure if "leg swelling" is definitely not present, then that factor may be removed at 867 also resulting in another recomputation. The clinician may turn off the microphone and transcription software by clicking icon 892.

Figure 5:
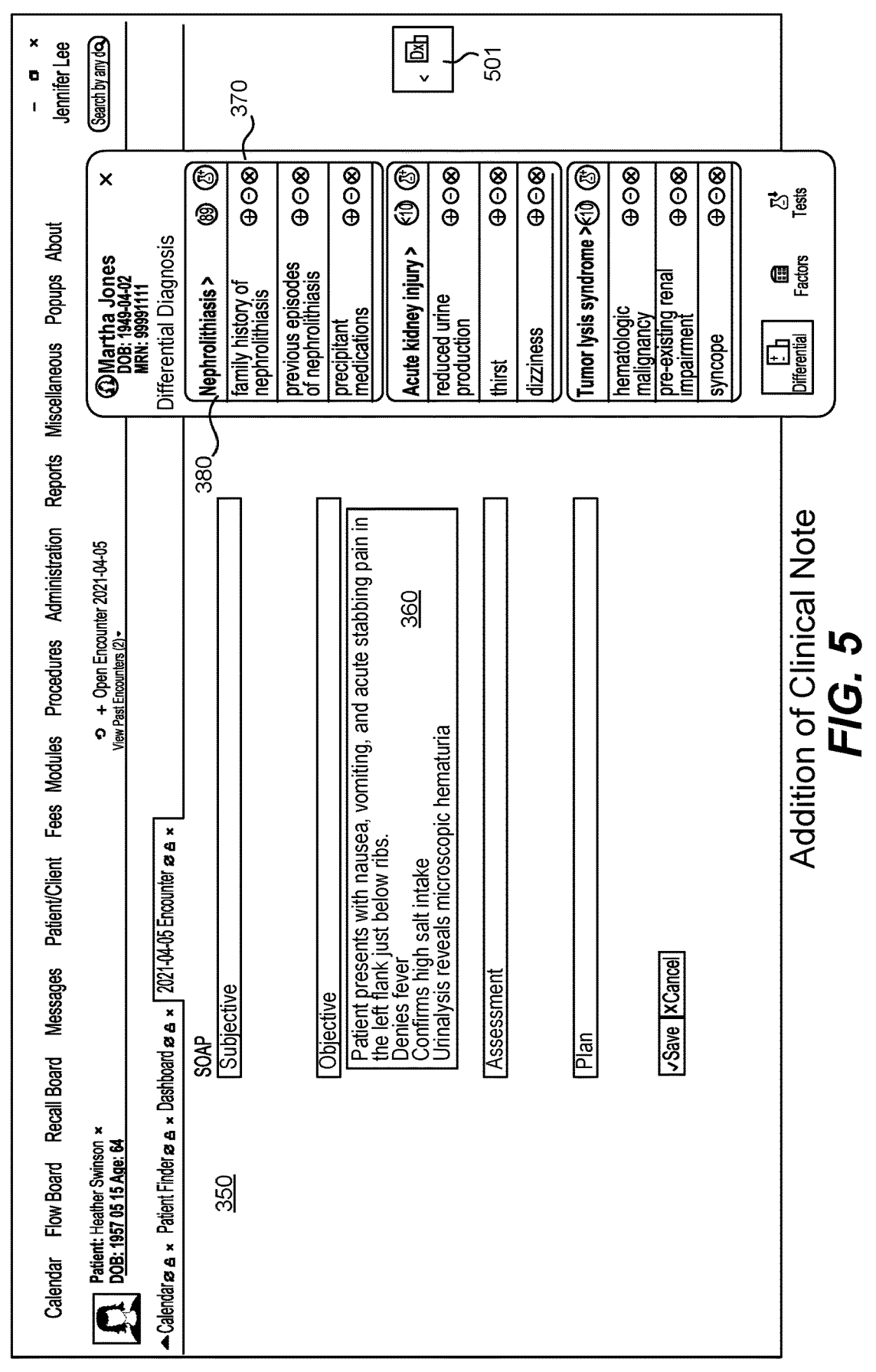

FIG. 5 illustrates a further example of the interaction between a clinician and the next-best-action system 10 in which the clinician enters a clinical note during a patient encounter. As shown, the clinician has started to enter her observations into a standard SOAP note, the contents of which is automatically read, to produce, based upon the clinical factors extracted, a highly probable differential diagnoses of nephrolithiasis. Shown is interface 350, the entered note 360, and window 370 showing the differential diagnoses as discussed above which are produced based upon the entered note.

Other Embodiments

The invention also includes the following embodiments.

E1. A system for displaying next best actions for patient care, said system comprising:

an information extraction engine arranged to receive from an electronic health record (EHR) system electronic text of a patient, said information extraction engine including at least a first trained computer model arranged to extract from said electronic text a plurality of patient diagnostic factors, each patient diagnostic factor known to be present or absent in said patient;

a factor probability matrix including sets of ranked diagnostic factors, each of said sets associated with a condition;

a condition ranker module arranged to match said patient diagnostic factors to said sets of ranked diagnostic factors in order to produce a list of at least one of said conditions;

a next-best-action engine arranged to determine, for each condition, a list of unknown diagnostic factors from the set of ranked diagnostic factors associated with said each condition that are not said patient diagnostic factors known to be present or absent in said patient; and a diagnostic user interface arranged to display on a computer screen said at least one of said conditions along with said determined list of unknown diagnostic factors ordered by the probability that each of said unknown diagnostic factors of said determined list indicates said at least one of said conditions.

F1. A system for displaying next best actions for patient care, said system comprising:

an information extraction engine arranged to receive from an electronic health record (EHR) system electronic text of a patient, said information extraction engine including at least a first trained computer model arranged to extract from said electronic text a plurality of performed treatments and a plurality of patient diagnostic factors, each patient diagnostic factor known to be present or absent in said patient;

a factor probability matrix including sets of ranked diagnostic factors, each of said sets associated with a condition;

a condition ranker module arranged to match said clinical diagnostic factors to said sets of ranked diagnostic factors in order to produce a list of at least one of said conditions;

a next-best-action engine arranged to determine, for each condition, a list of unperformed treatments that are not said performed treatments; and a diagnostic user interface arranged to display on a computer screen said at least one of said conditions along with said determined list of performed treatments ordered by the probability that each of said unperformed treatments of said determined list is cost effective against said at least one of said conditions.

G1. A system for displaying next best actions for patient care, said system comprising:

a speech recognition software module that transcribes a conversation between a clinician and a patient captured by at least one microphone to produce electronic text;

an information extraction engine arranged to receive from said speech recognition software module said electronic text, said information extraction engine including at least a first trained computer model arranged to extract from said electronic text a plurality of patient diagnostic factors, each patient diagnostic factor known to be present or absent in said patient;

a factor probability matrix including sets of ranked diagnostic factors, each of said sets associated with a condition;

a condition ranker module arranged to match said patient diagnostic factors to said sets of ranked diagnostic factors in order to produce a list of at least one of said conditions;

a next-best-action engine arranged to determine, for each condition, a list of unknown diagnostic factors from the set of ranked diagnostic factors associated with said each condition that are not said patient diagnostic factors known to be present or absent in said patient; and a diagnostic user interface arranged to display on a computer screen said at least one of said conditions along with said determined list of unknown diagnostic factors ordered by the probability that each of said unknown diagnostic factors of said determined list indicates said at least one of said conditions.

H1. A system for displaying next best actions for patient care, said system comprising:

a speech recognition software module that transcribes a conversation between a clinician and a patient captured by at least one microphone to produce electronic text;

an information extraction engine arranged to receive from said speech recognition software module said electronic text, said information extraction engine including at least a first trained computer model arranged to extract from said electronic text a plurality of performed treatments and a plurality of patient diagnostic factors, each clinical diagnostic factor known to be present or absent in said patient;

a factor probability matrix including sets of ranked diagnostic factors, each of said sets associated with a condition;

a condition ranker module arranged to match said patient diagnostic factors to said sets of ranked diagnostic factors in order to produce a list of at least one of said conditions;

a next-best-action engine arranged to determine, for each condition, a list of unperformed treatments that are not said performed treatments; and a diagnostic user interface arranged to display on a computer screen said at least one of said conditions along with said determined list of performed treatments ordered by the probability that each of said unperformed treatments of said determined list is cost effective against said at least one of said conditions.

A method as recited in claim 1, further comprising: including for each condition in said list a probability that said patient has said condition.

A method as recited in claim 10, further comprising: including for each condition in said list a probability that said patient has said condition.

A method as recited in claim 19, further comprising: including for each condition in said list a probability that said patient has said condition.

A method as recited in claim 25, further comprising: including for each condition in said list a probability that said patient has said condition.

Computer System Embodiment

Figure 11A:
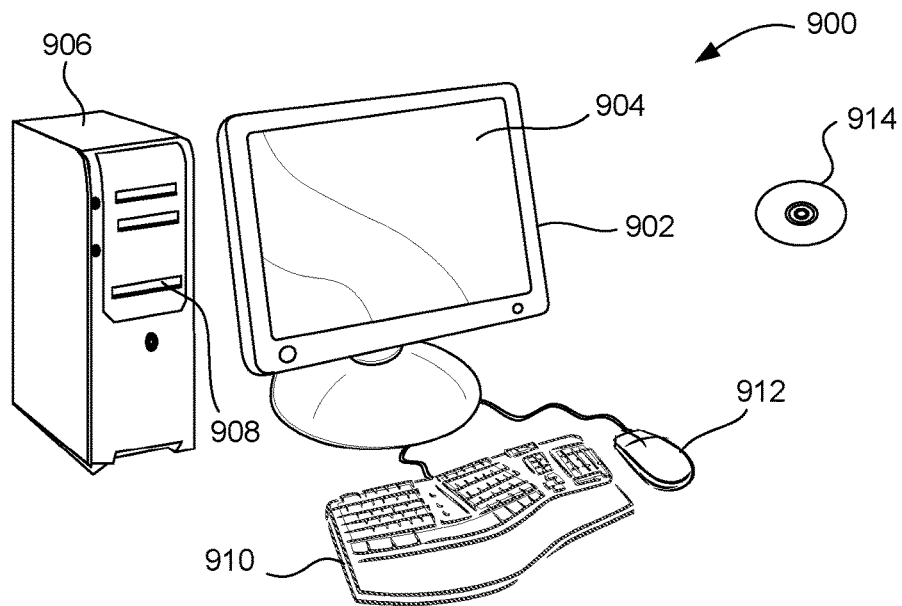
FIGS. 11A and 11B illustrate a computer system suitable for implementing embodiments of the present invention.
Figure 11B:
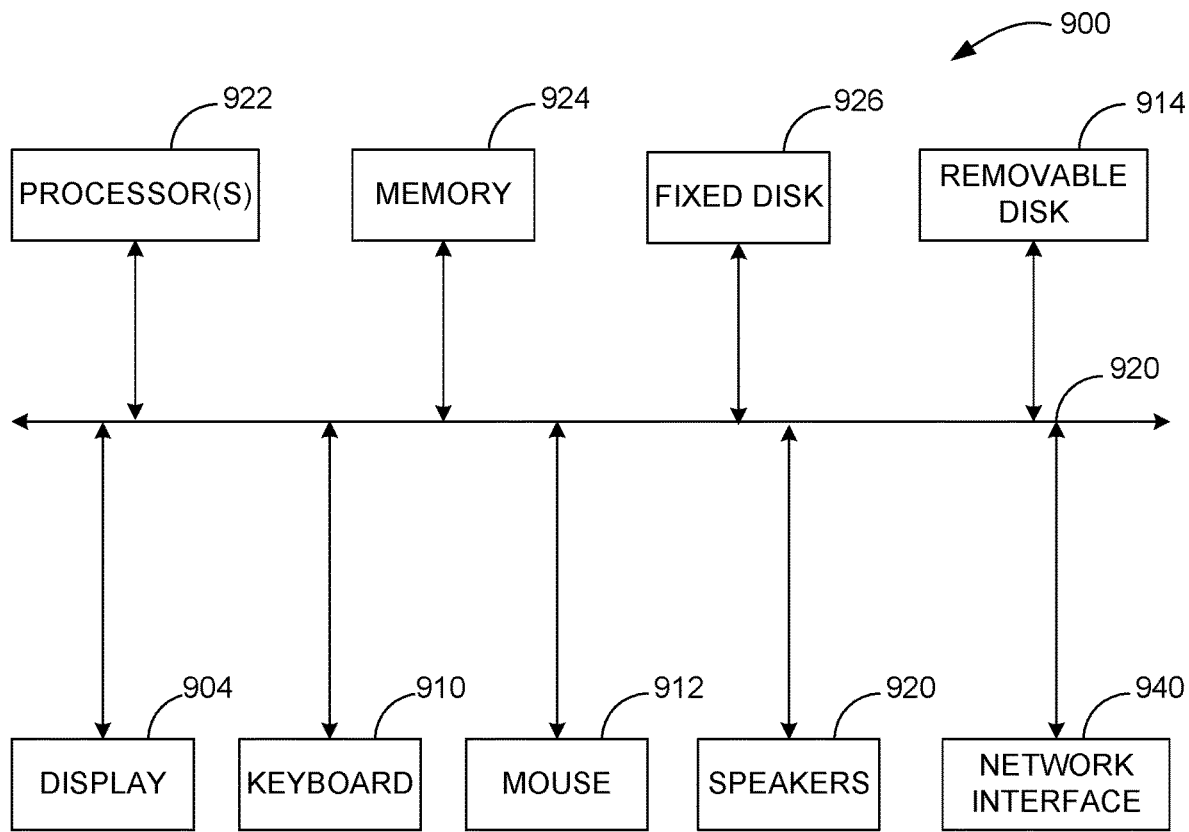

FIGS. 11A and 11B illustrate a computer system 900 suitable for implementing embodiments of the present invention. FIG. 11A shows one possible physical form of the computer system. Of course, the computer system may have many physical forms including an integrated circuit, a printed circuit board, a small handheld device (such as a mobile telephone or PDA), a personal computer or a super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 11B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary mass storage medium (such as a hard disk, a solid-state drive, a hybrid drive, flash memory, etc.) that can be slower than primary storage but persists data. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

We claim:

1. A method of displaying next best actions for patient care, said method comprising:
   a) receiving from an electronic health record (EHR) system electronic text of a patient medical record;
   b) using at least a first trained computer model, extracting from said electronic text a plurality of patient diagnostic factors, each patient diagnostic factor known to be present or absent in said patient;
   c) matching said patient diagnostic factors to sets of ranked diagnostic factors, each of said sets associated with a condition and each ranking of a diagnostic factor for its associated condition being a probability of said diagnostic factor being indicative of its associated condition, in order to produce a list of said conditions each having a probability of being present in said patient based upon said patient diagnostic factors, wherein said probability of each condition is a combination of said probabilities of said diagnostic factors associated with said each condition;
   d) determining, for each condition, a list of unknown diagnostic factors from the set of ranked diagnostic factors associated with said each condition that are not said patient diagnostic factors known to be present or absent in said patient;
   e) displaying on a computer screen at least one of said conditions with said probability of being present in said patient along with said determined list of unknown diagnostic factors ordered by the probability that each of said unknown diagnostic factors of said determined list is indicative of said at least one of said conditions; and
   f) after said displaying, receiving input indicating that one of said displayed unknown diagnostic factors is now known to be present or is now known to not be present.

2. A method as recited in claim 1 wherein each of said patient diagnostic factors is able to be observed by a clinician examining said patient or described by said patient to said clinician during an office visit.

3. A method as recited in claim 1 further comprising:
   extracting from said electronic text a plurality of performed tests;
   matching said performed tests to sets of ranked tests, each of said sets associated with a condition, in order to produce said list of at least one of said conditions;
   determining, for each condition, a second list of unperformed tests from the set of ranked tests associated with said each condition that are not said performed tests; and
   displaying on said computer screen along with said at least one of said conditions said determined second list of unperformed tests ordered by the probability that each of said unperformed tests of said determined list indicates said at least one of said conditions.

4. A method as recited in claim 1 wherein said patient diagnostic factors are laboratory tests, examinations or investigations that are unable to be performed during an office visit.

5. A method as recited in claim 1 further comprising:
   performing said displaying before a clinician-patient encounter begins.

6. A method as recited in claim 1 further comprising:
   after said displaying, receiving, from speech recognition software, electronic text of a conversation between a clinician and a patient captured by at least one microphone;
   performing steps b) through e) again using said electronic text received from said speech recognition software.

7. A method as recited in claim 1 further comprising:
   after said displaying, receiving new electronic text based upon a clinical note or diagnostic factor input into said EHR system by a clinician; and
   performing steps b) through e) again using said new electronic text.

8. A method as recited in claim 1, wherein said displaying is performed by a diagnostic user interface, said method further comprising:
   after said displaying, receiving via said diagnostic user interface input indicating that one of said displayed unknown diagnostic factors is now known to be present or is now known to not be present, receiving input that a present diagnostic factor is now known to be not present, or receiving input that a not present diagnostic factor is now known to be present; and
   performing steps b) through e) again using said input as said electronic text.

9. A method as recited in claim 1 wherein said probability (FR) of a diagnostic factor being indicative of its associated condition is given by the formula $$FR = r(E, L, R),$$

wherein "r" is a function that combines values E, L and R,
   wherein E is an evidence-based factor from 100% to 0% based on an evidence-based database,
   wherein L is a localized factor from 100% to 0% based on probability distributions from EHRs, and
   wherein R is a factor from 100% to 0% based on probability distributions from a sum of real world data.

10. A method of displaying next best actions for patient care, said method comprising:
    a) receiving from an electronic health record (EHR) system electronic text of a patient medical record;
    b) using at least a first trained computer model, extracting from said electronic text a plurality of performed treatments and a plurality of patient diagnostic factors, each patient diagnostic factor known to be present or absent in said patient;

c) matching said patient diagnostic factors to sets of ranked diagnostic factors, each of said sets associated with a condition and each ranking of a diagnostic factor for its associated condition being a probability of said diagnostic factor being indicative of its associated condition, in order to produce a list of said conditions each having a probability of being present in said patient based upon said patient diagnostic factors, wherein said probability of each condition is a combination of said probabilities of said diagnostic factors associated with said each condition;

d) determining, for each condition, a list of unperformed treatments that are not said performed treatments;

e) displaying on a computer screen at least one of said conditions with said probability of being present in said patient along with said determined list of unperformed treatments ordered by the probability that each of said unperformed treatments of said determined list is cost effective against said at least one of said conditions; and f) after said displaying, receiving input indicating that one of said displayed unperformed treatments has now been performed.

11. A method as recited in claim 10 wherein each of said patient diagnostic factors is able to be observed by a clinician examining said patient or described by said patient to said clinician during an office visit.

12. A method as recited in claim 10 further comprising:
extracting from said electronic text a plurality of performed tests; and
matching said performed tests to sets of ranked tests, each of said sets associated with a condition, in order to produce said list of at least one of said conditions.

13. A method as recited in claim 10 wherein said patient diagnostic factors are laboratory tests, examinations or investigations that are unable to be performed during an office visit.

14. A method as recited in claim 10 further comprising:
performing said displaying before a clinician-patient encounter begins.

15. A method as recited in claim 10 further comprising:
after said displaying, receiving, from speech recognition software, electronic text of a conversation between a clinician and a patient captured by at least one microphone;
performing steps b) through e) again using said electronic text received from said speech recognition software.

16. A method as recited in claim 10 further comprising:
only receiving said electronic text from said EHR system having a date later than an input date that is hardcoded into software, that is configured by an entity, or that is input by a clinician.

17. A method as recited in claim 10 further comprising:
after said displaying, receiving new electronic text based upon a clinical note or diagnostic factor input into said EHR system by a clinician; and
performing steps b) through e) again using said new electronic text.

18. A method as recited in claim 10, wherein said displaying is performed by a diagnostic user interface, said method further comprising:
after said displaying, receiving via said diagnostic user interface input indicating that one of said displayed unperformed treatments is now known to have been performed, receiving input that a present diagnostic factor is now known to be not present, or receiving input that a not present diagnostic factor is now known to be present; and
performing steps b) through e) again using said input as said electronic text.

19. A method of displaying next best actions for patient care, said method comprising:

a) receiving, from speech recognition software, electronic text of a conversation between a clinician and a patient captured by at least one microphone;

b) using at least a first trained computer model, extracting from said electronic text a plurality of patient diagnostic factors, each patient diagnostic factor known to be present or absent in said patient;

c) matching said patient diagnostic factors to sets of ranked diagnostic factors, each of said sets associated with a condition and each ranking of a diagnostic factor for its associated condition being a probability of said diagnostic factor being indicative of its associated condition, in order to produce a list of said conditions each having a probability of being present in said patient based upon said patient diagnostic factors, wherein said probability of each condition is a combination of said probabilities of said diagnostic factors associated with said each condition;

d) determining, for each condition, a list of unknown diagnostic factors from the set of ranked diagnostic factors associated with said each condition that are not said patient diagnostic factors known to be present or absent in said patient;

e) displaying on a computer screen at least one of said conditions with said probability of being present in said patient along with said determined list of unknown diagnostic factors ordered by the probability that each of said unknown diagnostic factors of said determined list is indicative of said at least one of said conditions; and f) after said displaying, receiving input indicating that one of said displayed unknown diagnostic factors is now known to be present or is now known to not be present.

20. A method as recited in claim 19 wherein each of said patient diagnostic factors is able to be observed by a clinician examining said patient or described by said patient to said clinician during an office visit.

21. A method as recited in claim 19 further comprising:
extracting from said electronic text a plurality of performed tests;
matching said performed tests to sets of ranked tests, each of said sets associated with a condition, in order to produce said list of at least one of said conditions;
determining, for each condition, a second list of unperformed tests from the set of ranked tests associated with said each condition that are not said performed tests;
displaying on said computer screen along with said at least one of said conditions said determined second list of unperformed tests ordered by the probability that each of said unperformed tests of said determined list indicates said at least one of said conditions.

22. A method as recited in claim 19 wherein said patient diagnostic factors are laboratory tests, examinations or investigations that are unable to be performed during an office visit.

23. A method as recited in claim 19 further comprising:
after said displaying, receiving new electronic text based upon a clinical note or diagnostic factor input into an EHR system by a clinician; and performing steps b) through e) again using said new electronic text.

24. A method as recited in claim 19, wherein said displaying is performed by a diagnostic user interface, said method further comprising:
after said displaying, receiving via said diagnostic user interface input indicating that one of said displayed unknown diagnostic factors is now known to be present or is now known to not be present, receiving input that a present diagnostic factor is now known to be not present, or receiving input that a not present diagnostic factor is now known to be present; and
performing steps b) through e) again using said input as said electronic text.

25. A method of displaying next best actions for patient care, said method comprising:
receiving, from speech recognition software, electronic text of conversation between a clinician and a patient captured by at least one microphone;
using at least a first trained computer model, extracting from said electronic text a plurality of performed treatments and a plurality of patient diagnostic factors, each patient diagnostic factor known to be present or absent in said patient;
matching said patient diagnostic factors to sets of ranked diagnostic factors, each of said sets associated with a condition and each ranking of a diagnostic factor for its associated condition being a probability of said diagnostic factor being indicative of its associated condition, in order to produce a list of said conditions each having a probability of being present in said patient based upon said patient diagnostic factors, wherein said probability of each condition is a combination of said probabilities of said diagnostic factors associated with said each condition;
determining, for each condition, a list of unperformed treatments that are not said performed treatments;
displaying on a computer screen at least one of said conditions with said probability of being present in said patient along with said determined list of unperformed treatments ordered by the probability that each of said unperformed treatments of said determined list is cost effective against said at least one of said conditions; and
after said displaying, receiving input indicating that one of said displayed unperformed treatments has now been performed.

26. A method as recited in claim 25 wherein each of said patient diagnostic factors is able to be observed by a clinician examining said patient or described by said patient to said clinician during an office visit.

27. A method as recited in claim 25 further comprising:
extracting from said electronic text a plurality of performed tests; and
matching said performed tests to sets of ranked tests, each of said sets associated with a condition, in order to produce said list of at least one of said conditions.

28. A method as recited in claim 25 wherein said patient diagnostic factors are laboratory tests, examinations or investigations that are unable to be performed during an office visit.

29. A method as recited in claim 25 further comprising:
after said displaying, receiving new electronic text based upon a clinical note or diagnostic factor input into said EHR system by a clinician; and
performing steps b) through e) again using said new electronic text.

30. A method as recited in claim 25, wherein said displaying is performed by a diagnostic user interface, said method further comprising:
after said displaying, receiving via said diagnostic user interface input indicating that one of said displayed unperformed treatments is now known to have been performed, receiving input that a present diagnostic factor is now known to be not present, or receiving input that a not present diagnostic factor is now known to be present; and
performing the second through fifth steps of claim 25 again using said input as said electronic text.

* * * * *